US010369360B2

(12) United States Patent
Arora et al.

(10) Patent No.: US 10,369,360 B2
(45) Date of Patent: Aug. 6, 2019

(54) DEVICES FOR MATERIAL DELIVERY, ELECTROPORATION, SONOPORATION, AND/OR MONITORING ELECTROPHYSIOLOGICAL ACTIVITY

(71) Applicant: Northwestern University, Evanston, IL (US)

(72) Inventors: Rishi Arora, Chicago, IL (US); Alan Kadish, Evanston, IL (US); Jason Ng, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/706,257

(22) Filed: Sep. 15, 2017

(65) Prior Publication Data

US 2018/0193639 A1    Jul. 12, 2018

Related U.S. Application Data

(63) Continuation of application No. 13/080,755, filed on Apr. 6, 2011, now abandoned, which is a (Continued)

(51) Int. Cl.
*A61N 1/32* (2006.01)
*A61N 1/04* (2006.01)
*A61N 1/20* (2006.01)

(52) U.S. Cl.
CPC ........... *A61N 1/327* (2013.01); *A61N 1/0412* (2013.01); *A61N 1/20* (2013.01)

(58) Field of Classification Search
CPC .... A61N 1/0412; A61N 1/0416; A61N 1/042; A61N 1/0424; A61N 1/0428;
(Continued)

(56) References Cited

U.S. PATENT DOCUMENTS

| 5,171,215 A | 12/1992 | Flanagan |
| 5,273,525 A | 12/1993 | Hofmann |

(Continued)

FOREIGN PATENT DOCUMENTS

| WO | WO 2002/087684 | 11/2002 |
| WO | WO 2007/130634 | 11/2007 |

OTHER PUBLICATIONS

Arora et al., 2007, "Targeted G-Protein Inhibition in the Posterior Left Atrium—A Novel Method to Selectively Inhibit Parasympathetic Signaling in the Left Atrium", Heart Rhythm 4(5S):S9.
(Continued)

*Primary Examiner* — Kami A Bosworth
(74) *Attorney, Agent, or Firm* — Casimir Jones, S.C.; David W. Staple

(57) ABSTRACT

The invention relates generally to systems and devices for material delivery, energy delivery, and/or monitoring electrophysiological activity, and method of use thereof. In particular, the present invention provides devices and systems, and methods of use thereof, configured to deliver therapeutic compositions, to provide electroporation and/or sonoporation to increase therapeutic efficiency, and to monitor electrophysiological activity, for example, before and after treatment.

3 Claims, 14 Drawing Sheets

Related U.S. Application Data continuation-in-part of application No. 12/959,864, filed on Dec. 3, 2010, now abandoned.

(60) Provisional application No. 61/266,280, filed on Dec. 3, 2009.

(58) Field of Classification Search
CPC .... A61N 1/0432; A61N 1/0436; A61N 1/044; A61N 1/0444; A61N 1/0448; A61N 1/20; A61N 1/30; A61N 1/303; A61N 1/306; A61N 1/325; A61N 1/327; A61N 1/056–0597
See application file for complete search history.

(56) References Cited

U.S. PATENT DOCUMENTS

| | | | |
|---|---|---|---|
| 5,571,159 A | 11/1996 | Alt | |
| 5,656,029 A | 8/1997 | Imran et al. | |
| 5,681,308 A | 10/1997 | Edwards et al. | |
| 5,697,965 A | 12/1997 | Griffin, III | |
| 5,928,269 A | 7/1999 | Alt | |
| 6,022,316 A | 2/2000 | Eppstein et al. | |
| 6,041,253 A | 3/2000 | Kost et al. | |
| 6,425,877 B1 | 7/2002 | Edwards | |
| 6,440,102 B1 | 8/2002 | Arenberg et al. | |
| 7,549,974 B2 | 6/2009 | Nayak | |
| 7,643,877 B2 | 1/2010 | Dujmovic, Jr. et al. | |
| 7,951,137 B2* | 5/2011 | Mehra | A61M 5/14244 600/516 |
| 8,512,219 B2 | 8/2013 | Ferren et al. | |
| 2002/0072089 A1* | 6/2002 | Holtzman | C07K 14/47 435/69.1 |
| 2004/0153134 A1 | 8/2004 | Fuimaono et al. | |
| 2005/0261672 A1 | 11/2005 | Deem et al. | |
| 2007/0066957 A1 | 3/2007 | Demarais et al. | |
| 2007/0088244 A1 | 4/2007 | Miller et al. | |
| 2007/0179535 A1 | 8/2007 | Morrissey et al. | |
| 2008/0021369 A1 | 1/2008 | Deem et al. | |
| 2008/0281314 A1 | 11/2008 | Johnson et al. | |
| 2009/0281019 A1 | 11/2009 | Arora et al. | |
| 2010/0081987 A1 | 4/2010 | Christian | |
| 2010/0112081 A1 | 5/2010 | Mishra et al. | |
| 2011/0104128 A1 | 5/2011 | Cooper et al. | |
| 2011/0245756 A1 | 10/2011 | Arora et al. | |

OTHER PUBLICATIONS

Arora et al., 2008, "Targeted G-Protein Inhibition in the Posterior Left Atrium—A Novel Gene-Based Approach to Selectively Inhibit Parasympathetic Signaling in the Left Atrium and Decrease Vagal AF Substrate," Heart Rhythm, 5(5S):S55.

Dean et al., 2003, "Electroporation as a method for high-level nonviral gene transfer to the lung," Gene Therapy, 10(18):1608-1615.

Dean et al., 2005, "Electroporation-mediated Gene Transfer of the Na+,K+-ATPase Resuces Endoctoxin-induced Lung Injury," Am J Physiol Cell Physiol, 289(2):C233-245.

Donahue, 2007, "Gene Therapy for Cardiac Arryhthmias: A Dream Soon to Come True?" J Cardiovascular Electrophysiology, 18(5):553-559.

Wells, 2010, "Electroporation and ultrasound enhanced non-viral gene delivery in vitro and in vivo," Cell Biol Toxicol., 26(1):21-8.

Yoon and Park, 2010, "Ultrasound-mediated gene delivery," Epert Opin Drug Deliv, 7(3):321-30.

Young and Dean, "Electroporation-Mediated Gene Delivery," Advances om Genetics, vol. 89, Ch. 3, pp. 49-88, 2015.

* cited by examiner

FIG. 2A
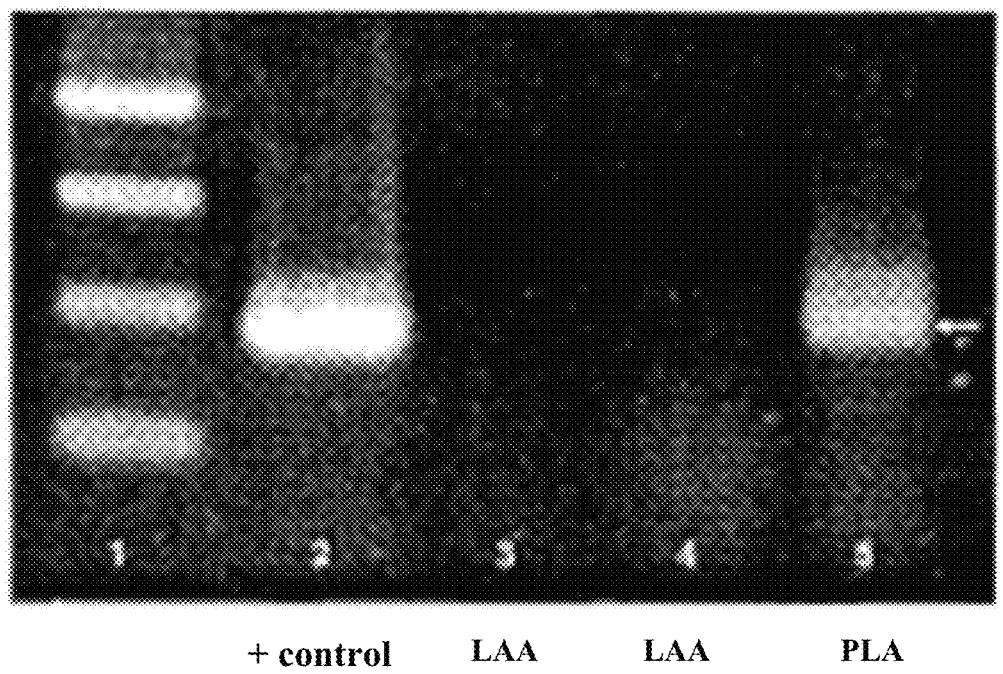
+ control    LAA    LAA    PLA
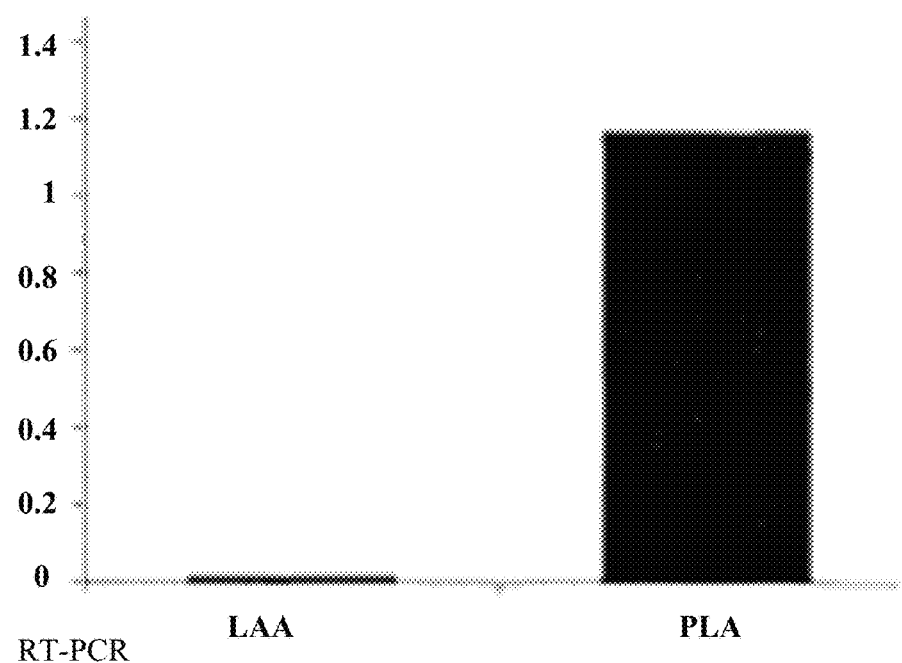
FIG. 2B

DEVICES FOR MATERIAL DELIVERY, ELECTROPORATION, SONOPORATION, AND/OR MONITORING ELECTROPHYSIOLOGICAL ACTIVITY

CROSS-REFERENCE TO RELATED APPLICATION

The present application is a continuation of U.S. patent application Ser. No. 13/080,755, filed Apr. 6, 2011, which is a continuation-in-part of U.S. patent application Ser. No. 12/959,864, filed Dec. 3, 2010, now abandoned, which claims priority to U.S. Provisional Application 61/266,280, filed Dec. 3, 2009, each of which is herein incorporated by reference in its entirety.

STATEMENT REGARDING FEDERALLY SPONSORED RESEARCH OR DEVELOPMENT

This invention was made with government support under Grant No. K08 HL074192 awarded by the National Institutes of Health, the National Heart, Lung, and Blood Institute. The government has certain rights in the invention.

FIELD OF THE INVENTION

The invention relates generally to systems and devices for material delivery, energy delivery, and/or monitoring electrophysiological activity, and method of use thereof. In particular, the present invention provides devices and systems, and methods of use thereof, configured to deliver therapeutic compositions, to provide electroporation and/or sonoporation to increase therapeutic efficiency, and to monitor electrophysiological activity, for example, before and after treatment.

BACKGROUND OF THE INVENTION

Gene-based approaches have been used to treat or palliate a variety of disease processes. For example, attempts have been made to use a gene-based approach to target rhythm disorders of the heart (e.g. atrial fibrillation) (AF) (Arora et al. Heart Rhythm. 2008; 5(5S):S55., herein incorporated by reference in its entirety). However, targeting a gene 'cargo' to an organ of interest presents a variety of challenges. (Dean et al. Am J Physiol Cell Physiol. August 2005; 289(2):C233-245., Dean et al. Gene therapy. September 2003; 1 0(18): 1608-1615., Donahue. Journal of cardiovascular electrophysiology. May 2007; 18(5):553-559, herein incorporated by reference in their entireties) Systemic gene delivery often results in sub-therapeutic concentrations of a gene in the organ of interest. In addition, systemic delivery carries the risk of unwarranted gene expression in organs that are remote from the region of interest, with the potential for significant side effects.

Catheter systems for local delivery of therapeutic agents have many advantages. Approaches for local delivery of agents at a depth within a tissue are applicable to the heart, pancreas, esophagus, stomach, colon, large intestine, and other tissues which may be accessed via a catheter system. These catheter systems will deliver drugs to the sites where they are most needed, reduce the amount of drug required, increase the therapeutic index, and control the time course of agent delivery. These, in turn, improve the viability of the drugs, lower the amount (and cost) of agents, reduce systemic effects, reduce the chance of drug-drug interactions, lower the risk to patients, and allow the physician to more precisely control the effects induced. Such local delivery may mimic endogenous modes of release, and address the issues of agent toxicity and short half lives.

AF is the most common sustained arrhythmia disturbance, occurring in 0.4% of the general population and in up to 40% of patients with congestive heart failure (CHF). It is a cause of significant morbidity (such as cerebrovascular embolism or 'stroke') and also contributes to increased mortality (Balasubramaniam & Kistler. Heart (British Cardiac Society). Jul. 16, 2008., herein incorporated by reference in its entirety). The diagnosis and management of AF have therefore become an important and challenging aspect of cardiovascular medicine. Unfortunately, current approaches to cure this arrhythmia are inadequate (Gerstenfeld et al. Heart Rhythm. February 2006; 3(2): 165-170., herein incorporated by reference in its entirety). The posterior left atrium (PLA) has been shown to play a significant role in the genesis of AF (Haissaguerre et al. Circulation. Mar. 28, 2000; 1 01 (12): 1409-1417., Haissaguerre et al. The New England Journal of Medicine. Sep. 3, 1998; 339(10):659-666, herein incorporated by reference in their entireties). This region has been shown to possess unique structural and electrophysiological characteristics that appear to contribute to substrate for AF. Both sympathetic and parasympathetic activity in the heart is mediated by heterotrimeric G-protein ($G\alpha G\alpha 3 G\alpha$) coupled pathways initiated by G-protein coupled receptors (GPCRs). A gene-based approach can be used to selectively inhibit the G-protein signaling pathways that are critical to autonomic signaling in the atrium (Arora et al. Heart Rhythm. 2007; 4(5S):S9., Arora et al. Heart Rhythm. 2008; 5(5S):S55., herein incorporated by reference in their entireties).

SUMMARY OF THE INVENTION

In some embodiments, the present invention provides a device comprising: (a) an elongate member with an inner lumen configured for delivery of a therapeutic agent to a treatment site within a subject, (b) an energy-delivery element configured to deliver energy to the treatment site within a subject, and (c) an electrophysiology monitoring element configured to monitor electrical signals (e.g. at or around the treatment site within said subject, such as the heart (e.g., epicardium, endocardium, etc.) or other organs, organ systems, and body systems. In some embodiments, an energy-delivery element is an electroporation element and/or a sonoporation element. In some embodiments, the present invention provides a device comprising: (a) an elongate member with an inner lumen configured for delivery of a therapeutic agent to a treatment site within a subject, and (b) an energy-delivery element (e.g., an electroporation element, a sonoporation element, etc.) configured to deliver energy (e.g., electric current, sound waves, ultrasonic energy, etc.) to the treatment site within a subject. In some embodiments, the present invention provides a device comprising: (a) an elongate member with an inner lumen configured for delivery of a therapeutic agent to a treatment site within a subject, and (b) an electrophysiology monitoring element configured to monitor and/or record electrical signals. In some embodiments, the present invention provides a device comprising: (a) an electrophysiology monitoring element configured to monitor electrical signals and (b) an energy-delivery element (e.g., an electroporation element, a sonoporation element, etc.) configured to deliver energy (e.g., electric current, sound waves, ultrasonic energy, etc.) to the treatment site within a subject. In some embodiments, the energy-delivery element (e.g., an electroporation element, a sonoporation element, etc.) is located at the distal tip of the device (e.g., at or near the distal end of the elongate member). In some embodiments, the energy-delivery element (e.g., an electroporation element, a sonoporation element, etc.) comprises one or more electroporation electrodes (e.g., which may be at or near the end of the elongate member). In some embodiments, the energy-delivery element (e.g., an electroporation element, a sonoporation element, etc.) comprises a plurality of electroporation electrodes (e.g., which may be at or near the end of the elongate member). In some embodiments, the energy-delivery element (e.g., an electroporation element, a sonoporation element, etc.) comprises one or more sonoporation elements, sonoporators, ultrasound generators, piezoelectric transducers (e.g., which may be at or near the end of the elongate member). In some embodiments, the electrophysiology monitoring element comprises a plurality of recording electrodes. In some embodiments, the plurality of monitoring electrodes comprises one or more distal monitoring electrodes and one or more proximal monitoring electrodes. In some embodiments, the device further comprises a handle located at the proximal end of the device. In some embodiments, the handle comprises one or more control elements. In some embodiments, the handle comprises one or more injection ports in fluid communication with the inner lumen. In some embodiments, the injection ports are configured for the loading therapeutic agents into the inner lumen. In some embodiments, a device comprises an inflatable and deflatable balloon element located at the distal tip of the elongate member. In some embodiments, the energy-delivery element (e.g., an electroporation element, a sonoporation element, etc.) is located on the balloon element. In some embodiments, the energy-delivery element (e.g., an electroporation element, a sonoporation element, etc.) comprises piezoelectric crystals configured to generate ultrasound energy. In some embodiments, the energy-delivery element (e.g., an electroporation element, a sonoporation element, etc.) comprises electrodes mounted and/or housed in and/or on the balloon element. In some embodiments, the electrophysiology monitoring element is located in and/or on said balloon element.

In some embodiments, the present invention provides a device comprising: (a) an elongate member configured for providing access to a treatment site within a subject, (b) an energy-delivery element configured to deliver energy to the treatment site within a subject, and (c) an electrophysiology monitoring element configured to monitor electrical signals (e.g. at or around the treatment site within said subject, such as the heart (e.g., epicardium, endocardium, etc.) or other organs, organ systems, and body systems. In some embodiments, an energy-delivery element is an electroporation element and/or a sonoporation element. In some embodiments, the elongate member comprises an inner lumen (e.g., for materials delivery). In some embodiments, the present invention provides a device comprising: (a) an elongate member configured for providing access to a treatment site within a subject, and (b) an energy-delivery element configured to deliver energy to the treatment site within a subject. In some embodiments, the present invention provides a device comprising: (a) an elongate member configured for providing access to a treatment site within a subject, and (b) an electrophysiology monitoring element configured to monitor electrical signals (e.g. at or around the treatment site within said subject, such as the heart (e.g., epicardium, endocardium, etc.) or other organs, organ systems, and body systems.

In some embodiments, the present invention provides a system comprising 1) a material delivery device, wherein said device comprises an elongate structure configured to access a treatment site within a subject and deliver physical material (e.g., therapeutic agent (e.g., nucleic acid)) to that site; and 2) an energy deliver/monitoring device comprising (a) an elongate member configured for providing access to a treatment site within a subject, (b) an energy-delivery element configured to deliver energy to the treatment site within a subject, and (c) an electrophysiology monitoring element configured to monitor electrical signals (e.g. at or around the treatment site within said subject, such as the heart (e.g., epicardium, endocardium, etc.) or other organs, organ systems, and body systems. In some embodiments, a material delivery device comprises an inner lumen through which material (e.g., therapeutic agent (e.g., nucleic acid)) can pass. In some embodiments, a material delivery device comprises a catheter. In some embodiments, the present invention provides methods for treating a subject wherein (a) a material delivery device is used to deliver therapeutic material (e.g., nucleic acids) to a treatment site (e.g. the heart or other organ systems); and (b) an energy deliver/monitoring device delivers energy (e.g., electric, ultrasound, etc.) to the treatment site to enhance the therapeutic effect of the therapeutic material. In some embodiments, a first device provides delivery of a therapeutic agent to a site within a subject (e.g., heart (e.g., epicardium, endocardium) or other tissue or organ system) and a second device provides sonoporation or electroporation to enhance the therapeutic effect of the therapeutic agent.

In some embodiments, the present invention provides a method of treating a disease or condition in a subject comprising: (a) inserting a catheter into the subject and placing the distal end of the catheter at or near a treatment site, (b) delivering a therapeutic agent to the treatment site through the lumen of the catheter, and (c) electroporating and/or sonoporating the treatment site with energy-delivery elements (e.g., an electroporation element, a sonoporation element, etc.) located on the distal end of the catheter (e.g., such that cells at the treatment site are transfected with reagents delivered via the catheter). In some embodiments, a treatment site is electroporated but not sonoporated. In some embodiments, a treatment site is sonoporated but not electroporated. In some embodiments, a treatment site is electroporated and sonoporated. In some embodiments, the method further comprises an initial step of monitoring electrical signals at the treatment site with an electrophysiology monitoring element. In some embodiments, the method further comprises (d) monitoring electrical signals at the treatment site with an electrophysiology monitoring element. In some embodiments, the method further comprises (e) comparing electrical signals from the initial step with electrical signals of step (d). In some embodiments, the method further comprises (f) determining the effectiveness of the treating based on comparison of the electrical signals from the initial step with electrical signals of step (d). In some embodiments, the therapeutic agent comprises gene therapy reagents. In some embodiments, the gene therapy reagents comprise nucleic acids (e.g., plasmids or AAV vectors comprising a gene of interest). In some embodiments, the nucleic acids comprise DNA. In some embodiments, the DNA comprises one or more mini-genes.

In some embodiments, the present invention provides a method of treating a disease or condition in a subject comprising: (a) delivering a therapeutic agent to s treatment site within a subject (e.g., cardiac tissue (e.g., epicardium, endocardium) or other non-cardiac tissues and body systems), and (b) electroporating and/or sonoporating the treatment site with an energy-delivery element (e.g., an electroporation element, a sonoporation element, etc.) such that cells at the treatment site are transfected with the thereapeutic agents. In some embodiments, the therapeutic agent and electroporation/sonoporation energy are delivered to the treatment site through a single device. In some embodiments, the therapeutic agent and electroporation/sonoporation energy are delivered to the treatment site through separate devices. In some embodiments, the present invention provides a method of treating a disease or condition in a subject comprising: (a) delivering a therapeutic agent to s treatment site within a subject (e.g., cardiac tissue (e.g., epicardium, endocardium) or other non-cardiac tissues and body systems), (b) electroporating and/or sonoporating the treatment site with an energy-delivery element (e.g., an electroporation element, a sonoporation element, etc.) such that cells at the treatment site are transfected with the thereapeutic agents, and (c) monitoring the electrophysiological activity at the treatment site (e.g., before and/or after treatment).

In some embodiments, the present invention comprises a system comprising: (a) an elongate member comprising an inner lumen, wherein said inner lumen is configured for delivery of a therapeutic agent to a treatment site within a subject, (b) an energy-delivery element (e.g., an electroporation element, a sonoporation element, etc.), wherein said energy-delivery element (e.g., an electroporation element, a sonoporation element, etc.) is configured to deliver energy (e.g., electric current, ultrasonic energy) to said treatment site within a subject, and (c) an electrophysiology monitoring element, wherein said electrophysiology monitoring element is configured to monitor electrical signals (e.g., in an around the treatment site in order to guide the device). In some embodiments, a system provides an elongate member with an inner lumen and energy-delivery element (e.g., an electroporation element, a sonoporation element, etc.) element. In some embodiments, a system comprises an elongate member with an inner lumen and an electrophysiology monitoring element. In some embodiments, a system comprises an energy-delivery element (e.g., an electroporation element, a sonoporation element, etc.) and an electrophysiology monitoring element. In some embodiments, the energy-delivery element (e.g., an electroporation element, a sonoporation element, etc.) is located at the distal tip of the system. In some embodiments, the energy-delivery element (e.g., an electroporation element, a sonoporation element, etc.) comprises a plurality of electroporation electrodes. In some embodiments, the electrophysiology recording element comprises a plurality of monitoring electrodes. In some embodiments, the plurality of monitoring electrodes comprises one or more distal monitoring electrodes and one or more proximal monitoring electrodes. In some embodiments, the system further comprises a handle located at the proximal end of the system. In some embodiments, the handle comprises one or more control elements. In some embodiments, the handle comprises one or more injection ports in fluid communication with the inner lumen. In some embodiments, the injection ports are configured for loading therapeutic agents into the inner lumen.

BRIEF DESCRIPTION OF THE DRAWINGS

The description provided herein is better understood when read in conjunction with the accompanying drawings which are included by way of example and not by way of limitation.

FIG. 2A shows the results of PCR on PLA tissue injected with exemplary gene therapy minigene.

FIG. 2B shows the results of RT-PCR demonstrating the expression of an injected miniene in the PLA, but not the LAA.

DEFINITIONS

Figure 1:
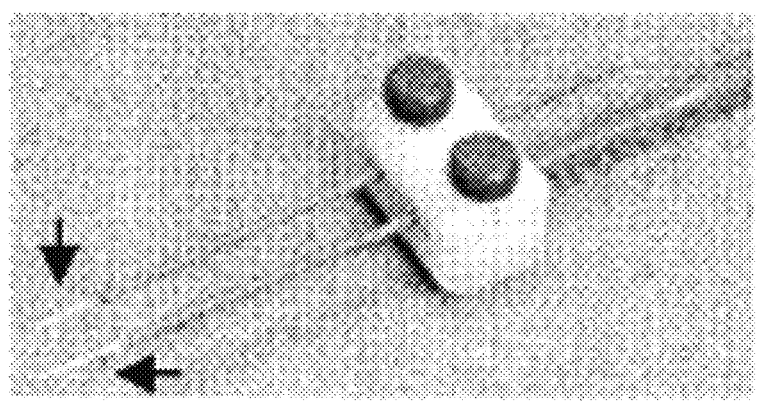
FIG. 1 shows exemplary electroporation electrodes.

As used herein, the term "subject" refers to any animal including, but not limited to, insects, humans, non-human primates, vertebrates, bovines, equines, felines, canines, pigs, rodents, and the like. The terms "subject" and "patient" may be used interchangeably, wherein the term "patient" generally refers to a subject seeking or receiving treatment or preventative measures from a clinician or health care provider. A subject may be of any stage of life (e.g. embryo, fetus, infant, neonatal, child, adult, live, dead, etc.).

As used herein, the term "effective amount" refers to the amount of a compound sufficient to effect beneficial or desired results. An effective amount can be administered in one or more administrations, applications or dosages and is not limited to or intended to be limited to a particular formulation or administration route.

As used herein, the term "pharmaceutical composition" refers to the combination of an active agent with a carrier, inert or active, making the composition especially suitable for diagnostic or therapeutic use in vivo, in vivo or ex vivo.

The term "gene therapy" is given its ordinary meaning in the art. Briefly, "gene therapy" refers to the transfer of genetic material (e.g., a DNA or RNA polynucleotide) of interest into a host cell and/or tissue to treat or prevent a disease condition. The genetic material of interest typically encodes a product whose in vivo production is desired. The genetic material of interest can also include various control elements, such as transcriptional promoters. It is noted that the end result of gene therapy does not have to always include a cure, but instead, also includes reducing the severity of one or more symptoms of a disease.

DETAILED DESCRIPTION

In some embodiments, the present invention provides catheter devices. In some embodiments, catheter devices are configured for material delivery, energy delivery (e.g. electroporation, ultrasound energy), and/or monitoring electrophysiological activity. In some embodiments, catheters are configured to deliver materials to a specific location within a subject (e.g. organ, portion of an organ, heart, artery, tissue, etc.). In some embodiments, catheters are configured to provide energy delivery energy (e.g., electric energy, ultrasonic energy, etc.), electroporation, or sonoporation (e.g., to facilitate or increase the efficiency of therapeutic uptake into cells). In some embodiments, catheters are configured to provide electric energy (e.g. to facilitate or increase the efficiency of therapeutic uptake into cells). In some embodiments, catheters are configured to provide ultrasound energy (e.g. to facilitate or increase the efficiency of therapeutic uptake into cells). In some embodiments, the present invention is configured to monitor physiological electric signals or impulses. In some embodiments, the present invention is configured to record intracardiac electrophysiologic activity (e.g. electrocardiogram). In some embodiments, a single catheter is configured to perform two or more functions of the present invention, e.g., therapeutic-agent delivery, energy delivery (e.g., sonoporation, electroporation, etc.), accessing a treatment site within a subject, electrophysiological monitoring, etc. In some embodiments, a system of the present invention comprises two or more devices configured to perform two or more functions of the present invention, e.g., therapeutic-agent delivery, energy delivery (e.g., sonoporation, electroporation, etc.), accessing a treatment site within a subject, electrophysiological monitoring, etc. In some embodiments, the present invention provides a device or system comprising (a) the ability to record and/or monitor electrical signals (e.g. in order to guide or determine the effectiveness of gene injection, electroporation, and/or ultrasound), (b) the ability to deliver a biologically active 'cargo' (e.g. naked DNA) (e.g. via a transvenous (transseptal) approach), and (c) the ability to perform electroporation and/or application of ultrasound energy (e.g. to facilitate intracellular gene transfer). In some embodiments, the present invention provides a system comprising a catheter with a lumen, energy-delivery element (e.g., electroporation element, sonoporation element, etc.), and an electrophysiology monitoring element.

In some embodiments, the present invention provides devices, systems, and methods to direct electroporation to target delivery sites within a subject. Electroporation, or electropermeabilization, is a significant increase in the electrical conductivity and permeability of the cell plasma membrane caused by an externally applied electrical field. In some embodiments, a device of the present invention directs an applied electric field toward a treatment site to aid in therapeutic (e.g., nucleic acid) uptake. In some embodiments, a device of the present invention directs an applied electric field toward a treatment site to destroy tissue and/or cells at the treatment site. In some embodiments, any suitable level of electric current can be delivered through a device of the present invention and applied to a site within a subject. In some embodiments, the level of electric current applied to a site (e.g. treatment site, delivery site, etc.) is selected based on the application (e.g., enhancement of therapeutic delivery, tissue ablation, etc.), subject (e.g., species, size, age, etc.), treatment site (e.g., epicardium, endocardium, non-cardiac tissue, etc.), and considerations known to those of skill in the art. In some embodiments, electric current is delivered continuously for a period of time (e.g., 1 second . . . 2 seconds . . . 5 seconds . . . 10 seconds . . . 30 seconds . . . 1 minute . . . 2 minutes . . . 5 minutes . . . 10 minutes . . . 30 minutes . . . 1 hour, or more). In some embodiments, electric current is pulsed. In some embodiments, the length of pulse, current applied, and duration of pulsing are selected based on appropriate criteria determined by a skilled artisan or clinician. In some embodiments, the level of electric current applied by a device of the present invention is between 0.01 Amp and 100 Amp (e.g., 0.01 Amp . . . 0.02 Amp . . . 0.05 Amp . . . 0.1 Amp . . . 0.2 Amp . . . 0.5 Amp . . . 1.0 Amp . . . 2.0 Amp . . . 5.0 Amp . . . 10 Amp . . . 20 Amp . . . 50 Amp . . . 100 Amp). In some embodiments, pulses are 0.1 seconds to 10 seconds in length (e.g., 0.1 s . . . 0.2 s . . . 0.5 s . . . 1 s . . . 2 s . . . 5 s . . . 10 s), and delivered for 1 s to 1 hour (e.g., 1 second . . . 2 seconds . . . 5 seconds . . . 30 seconds . . . 1 minute . . . 2 minutes . . . 5 minutes . . . 10 minutes . . . 30 minutes . . . 1 hour).

In some embodiments, the present invention provides devices, systems, and methods to direct sonoporation to target delivery sites within a subject. Sonoporation, or cellular sonication, is the use of sound (e.g., ultrasonic frequencies) for modifying the permeability of the cell plasma membrane. In some embodiments, a device of the present invention directs sonic energy (e.g., ultrasound frequencies) to a treatment site to aid in therapeutic (e.g., nucleic acid) uptake. In some embodiments, a device of the present invention directs an ultrasound (e.g., cyclic sound pressure) toward a treatment site to destroy tissue and/or cells at the treatment site. In some embodiments, any suitable level of ultrasound can be delivered through a device of the present invention and applied to a site within a subject. In some embodiments, the level and/or frequency of ultrasound applied to a site (e.g. treatment site, delivery site, etc.) is selected based on the application (e.g., enhancement of therapeutic delivery, tissue ablation, etc.), subject (e.g., species, size, age, etc.), treatment site (e.g., epicardium, endocardium, non-cardiac tissue, etc.), and considerations known to those of skill in the art. In some embodiments, ultrasound is delivered continuously for a period of time (e.g., 1 second . . . 2 seconds . . . 5 seconds . . . 10 seconds . . . 30 seconds . . . 1 minute . . . 2 minutes . . . 5 minutes . . . 10 minutes . . . 30 minutes . . . 1 hour, or more). In some embodiments, ultrasound is pulsed. In some embodiments, the length of pulse, level and/or frequency of ultrasound applied, and duration of pulsing are selected based on appropriate criteria determined by a skilled artisan or clinician. In some embodiments, the frequency of ultrasound applied by a device of the present invention is between 20 kHz and 200 MHz (e.g., 20 kHz . . . 50 kHz . . . 100 kHz . . . 200 kHz . . . 500 kHz . . . 1 MHz . . . 2 MHz . . . 5 MHz . . . 10 MHz . . . 20 MHz . . . 50 MHz . . . 100 MHz . . . 200 MHz). In some embodiments, the level of ultrasound applied by a device of the present invention has a mechanical index (MI) between 0.01 and 5 (e.g., 0.01 . . . 0.02 . . . 0.05 . . . 0.1 . . . 0.2 . . . 0.5 . . . 1.0 . . . 2.0 . . . 5.0). In some embodiments, pulses are 0.1 seconds to 10 seconds in length (e.g., 0.1 s . . . 0.2 s . . . 0.5 s . . . 1 s . . . 2 s . . . 5 s . . . 10 s), and delivered for 1 s to 1 hour (e.g., 1 second . . .

2 seconds . . . 5 seconds . . . 30 seconds . . . 1 minute . . . 2 minutes . . . 5 minutes . . . 10 minutes . . . 30 minutes . . . 1 hour).

Figure 12:
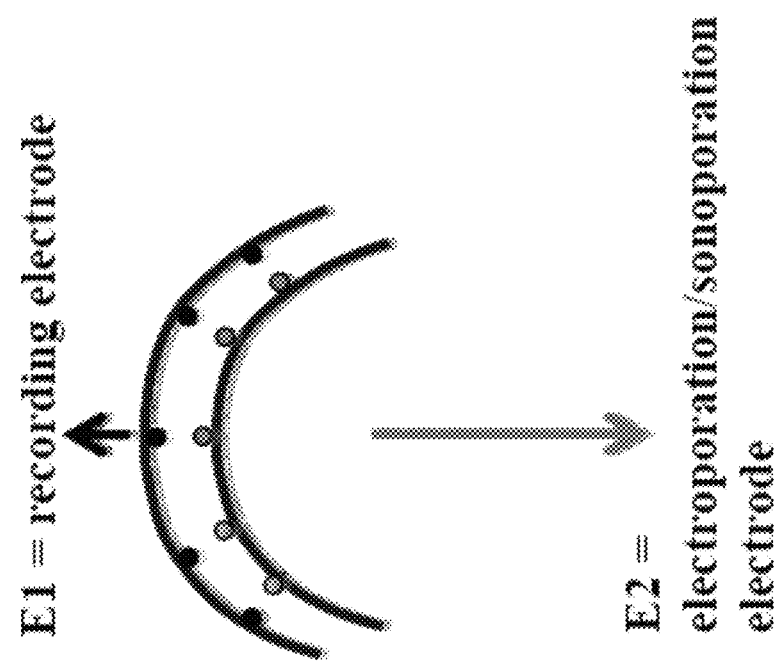
FIG. 12 shows a side view of an exemplary energy-delivery element. Recording electrodes and electroporation-and/or sonoporation-emitting elements are positioned along an energy-delivery element, e.g., to facilitate placement against a body tissue (e.g., epicardium, other cardiac surface, and/or other non-cardiac surface).
Figure 13:
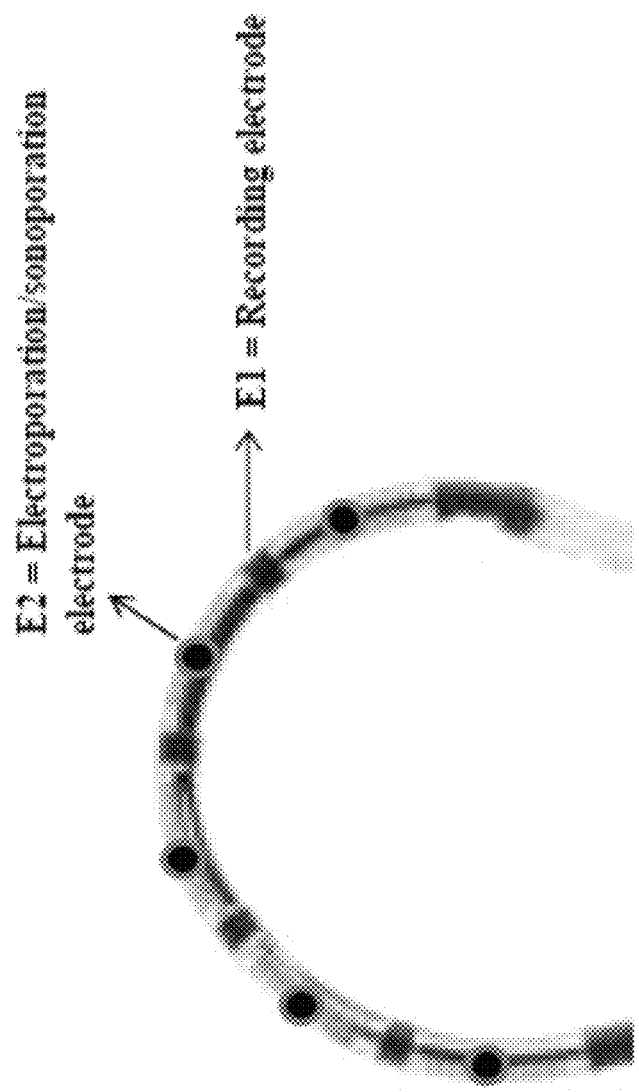
FIG. 13 shows a side view of an exemplary energy-delivery element. Recording electrodes and electroporation-and/or sonoporation-emitting elements are positioned along an energy-delivery element, e.g., to facilitate placement against a body tissue (e.g., epicardium, other cardiac surface, and/or other non-cardiac surface).

In some embodiments, an energy-delivery element is configured to emit energy from the terminal portion of the distal tip, thereby directing energy to a singular spot within the treatment site. In such embodiments, the size and/or shape of the area targeted by the emitted energy depends upon the size of the energy-delivery element, the shape of the energy-delivery element, and the trajectory of the emitted energy. In some embodiments, an energy-delivery element is configured to emit energy from a segment at or near the distal tip (e.g., the penultimate segment) (SEE, e.g., FIGS. 12 and 13), thereby directing energy to a region within the treatment site in contacted by the energy-delivery segment. In such embodiments, the size and/or shape of the area targeted by the emitted energy depends upon the arrangement of energy-emitting elements on the energy-delivery segment and the orientation of the energy-delivery segment on the treatment site. In some embodiments, an energy-delivery segment is a linear segment of an elongated device, wherein energy-delivery elements (e.g., sonoporation elements, electroporation elements, etc.) are arranged along the length of the segment. In some embodiments, electrophysiology monitoring elements are spaced along the same segment as the energy-delivery elements. In some embodiments, the length of an energy-delivery segment is positioned along the desired treatment site. In some embodiments, the length of an energy-delivery segment is clamped around a desired treatment site. In some embodiments, a device of the present invention is configured to position an energy-delivery element or energy-delivery segment to direct energy to a desired position or region of the treatment site. In some embodiments, one or more various positioning and stabilizing elements (e.g., clamp, balloon, clip, vacuum, etc.) are utilized to position an energy-delivery element or energy-delivery segment in the proper position on or within a treatment site.

In some embodiments, the present invention comprises an elongate member (e.g. a material-delivery/energy-delivery/electrophysiology catheter). In some embodiments, an elongate member is a catheter or other site-access element. In some embodiments, a catheter shaft is flexible (e.g., bendable). In some embodiments the catheter is flexible throughout its length. In some embodiments the catheter is flexible at its distal end. In some embodiments, the catheter is substantially non-compressible along its length. In some embodiments, the present invention comprises a delivery, electroporation, sonoporation (e.g., ultrasound), and/or electrophysiology catheter. In some embodiments, the outer wall comprises an imbedded braided mesh of stainless steel or the like, as is generally known in the art, to increase torsional stiffness of the catheter shaft so that, when the proximal catheter end is rotated, the distal catheter shaft will rotate in a corresponding manner. In some embodiments, torsional stiffness is achieved through other mechanisms known to those in the art. In some embodiments, the useful length of the catheter, e.g., that portion that can be inserted into the body, varies as desired. In some embodiments, the useful length ranges from about 30 cm to about 300 cm (e.g. 30 cm . . . 40 cm . . . 50 cm . . . 100 cm . . . 200 cm . . . 300 cm). In some embodiments, the diameter, circumference, and/or gauge of the catheter varies as desired. In some embodiments, useful outer diameters range from about 3-36 French (Fr) (e.g., 3 Fr, 4 Fr, 5 Fr, 6 Fr, 7 Fr, 8 Fr, 9 Fr, 10 Fr, 11 Fr, 12 Fr, 13 Fr, 14 Fr, 15 Fr, 16 Fr, 17 Fr, 18 Fr, 19 Fr, 20 Fr, 21 Fr, 22 Fr, 23 Fr, 24 Fr, 25 Fr, 26 Fr, 27 Fr, 28 Fr, 29 Fr, 30 Fr, 31 Fr, 32 Fr, 33 Fr, 34 Fr, 35 Fr, 36 Fr, or diameters therein). In some embodiments, catheter diameter varies throughout its length. In some embodiments, catheter diameter is constant throughout the length of the insertion portion or catheter shaft. In some embodiments, the catheter is steerable to allow for navigation within a subject or working environment (e.g. artery, vein, organ, etc.). In some embodiments, a catheter is steerable. In some embodiments, the catheter has bidirectional steerablity (e.g. the distal end of the catheter is configured to be bendable in the left/right plane via controls at the catheter handle), and/or rotational steerability (e.g. the distal end of the catheter is configured to have 360° bendability). One exemplary steerable catheter is described in U.S. Pat. No. 5,656,029, herein incorporated by reference in its entirety.

Optionally, a system may further include at least one visualization member for enhancing visualization of the treatment site (e.g., heart tissue). In some embodiments, for example, the visualization member may include an optic imaging device, a thermal imaging device, an ultrasound device, an electrical imaging device, a Doppler imaging device or the like, though any suitable device may be used.

Some embodiments of the invention also include at least one positioning device for contacting the treatment site (e.g., epicardium, endocardium, non-cardiac tissue, etc.) and positioning the device for treatment. For example, the positioning device may comprise a suction positioning device, positioning balloon, clamp, clip, etc.

In some embodiments, the energy-delivery element is coupled with at least one guiding member such that a change in shape of the guiding member causes a corresponding change in shape of the energy-delivery element. For example, the guiding member may comprise a deformable linear member its shape being adjustable by a user, and wherein the energy-delivery element comprises a deformable linear member (e.g., energy-delivery segment) coaxially coupled with the guiding member so as to move with the guiding member. In some embodiments, the guiding member is adjustable to at least partially encircle, abut, grasp, and/or sit adjacent to one or more selected tissues, organs, or portions thereof. In some embodiments, one or more clamps, balloons, and/or suction elements assist in positioning, deforming, and/or shaping an energy delivery element to adopt a desired position on/in a treatment site.

Optionally, a system may further include at least one needle coupled with the material-delivery element for insertion into the tissue (e.g., epidardium) to enhance application of the at least one therapeutic agent. The material-delivery element itself may comprise at least one needle and at least one aperture adjacent a tip of each needle for allowing passage of the at least one therapeutic agent out of the needle to contact the treatment site (e.g., heart tissue). Optionally, the needle may be retractable. For example, the retractable needle may be exposed and retracted via a pneumatic member coupled with the material-delivery element. In some embodiments, the retractable needle is exposed and retracted automatically when the material-delivery element the treatment site. In some embodiments, a depth of penetration of the retractable needle into the heart tissue is adjustable. In some embodiments, a needle is used in conjunction with an energy-delivery element (e.g., sonoporation element, electroporation element, etc.) to enhance therapeutic delivery within tissue (e.g., cardiac tissue, non-cardiac tissue).

Figure 9A:
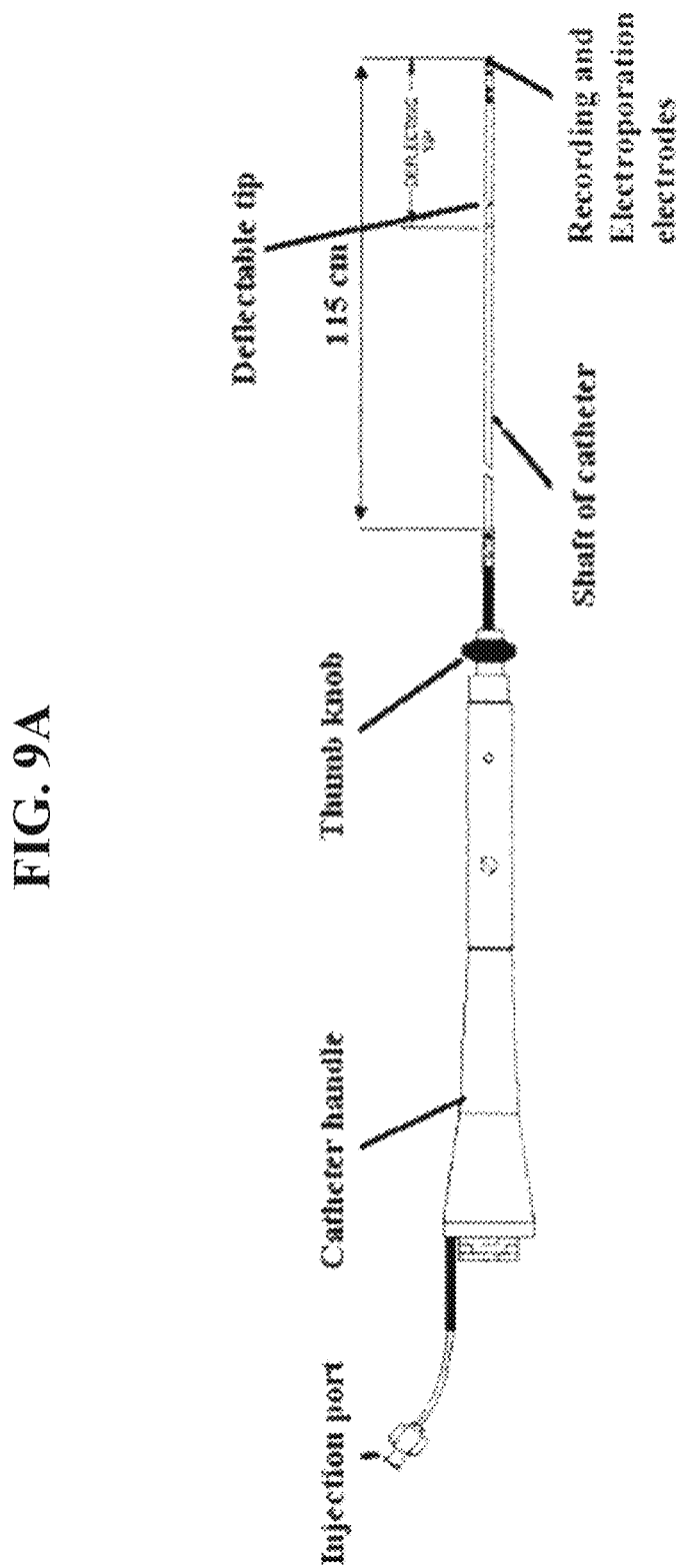
FIG. 9A an exemplary catheter device of the present invention.
Figure 9B:
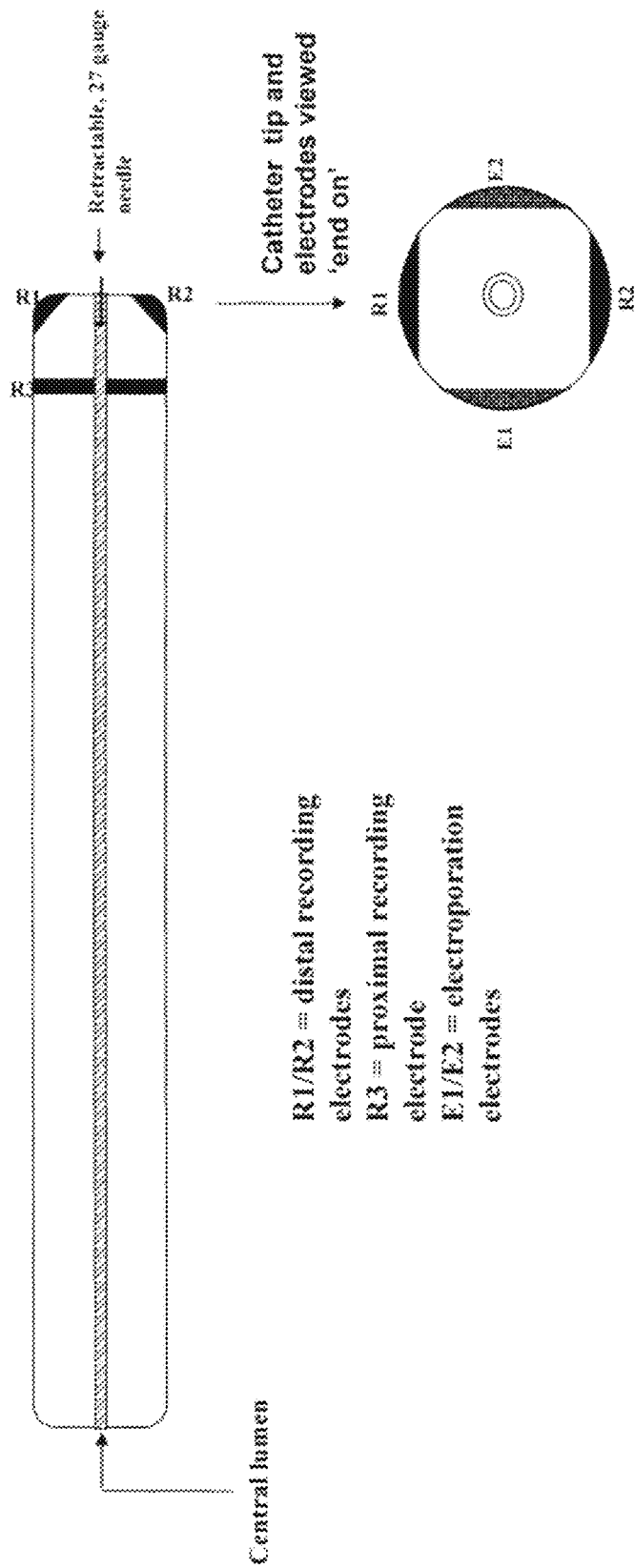
FIG. 9B shows an exemplary distal end of a catheter shaft of the present invention.

FIGS. 9A and 9B provide exemplary embodiments of the present invention. These embodiments should not be viewed as limiting the scope of the present invention. As shown in FIG. 9A, in some embodiments, the present invention comprises a handle portion and a shaft portion. The handle portion comprises an injection port, a means for holding the catheter by an operator, and controls for manipulating the catheter (e.g. thumb knob). The shaft portion, or shaft of the catheter, is the portion of the catheter which is inserted into, and maneuvered through a subject. The shaft may be of any suitable length and comprises a deflectable tip. In some embodiments, manipulation of the catheter handle by an operator allows for placement of the catheter shaft and the catheter tip into an appropriate location within a subject for localized treatment. As shown in FIG. 9B, the catheter shaft and catheter tip comprise at least one central lumen. In some embodiments, the catheter may comprise a plurality of lumens. Generally, the lumen runs the length of the catheter shaft and provides a means for delivering therapeutics to a treatment site. The lumen may also provide additional functions. In some embodiments, the distal tip and/or distal segment of the catheter comprises a plurality of electrodes (e.g., for electroporation). In some embodiments, the distal tip and/or distal segment of the catheter comprises one or more piezoelectric crystals or other ultrasound producing objects or devices (e.g., for sonoporation). In certain embodiments, the distal tip and/or distal segment of the catheter comprises both one or more recording/monitoring electrodes for measuring, monitoring and recoding electrophysiology signals, and one or more electroporation electrodes for delivering electrical current. In some embodiments, the distal tip and/or distal segment of the catheter comprises one or more recording/monitoring electrodes for measuring, monitoring and recoding electrophysiology signals, and one or more sonoporation elements (e.g., ultrasound generator, piezoelectric crystal, etc.) for delivering ultrasonic energy. In some embodiments, the distal tip and/or distal segment of the catheter comprises two types of monitoring electrodes: distal monitoring electrodes which are located on the ultimate end of the tip, and one or more proximal monitoring electrodes located at the catheter tip, but prior to the end. In some embodiments, electrodes are spaced around the distal tip and/or distal segment of the catheter. In some embodiments, the distal tip and/or distal segment of the catheter comprises elements for both sonoporation and electroporation. In some embodiments, the distal tip and/or distal segment of the catheter comprises elements for: 1) recording/monitoring electrophysiology, 2) sonoporation, and 3) electroporation.

In some embodiments, control of the catheter is provided by an integrated hand-held control mechanism and/or handle mounted on the proximal end of the catheter. In some embodiments, the control mechanism/handle can be of various types, and adapted for operating a steerable catheter wherein the bend of the catheter can be selectively controlled by the operator. In some embodiments, controls are an integral part of the handle portion of the catheter. In some embodiments, controls and/or steering mechanisms are part of a separate unit attached to, or operable connected to a catheter. In some embodiments, the mechanism/handle includes a set of controls, which allow the operator to control the steering of the catheter and other operational functions of the catheter (e.g. material injection/deposition, electroporation, sonoporation, electrophysiology measurements, etc.). It will be apparent to one of ordinary skill in the art that other control mechanisms/handles can be employed with the systems of the invention without departing from the scope thereof. Specifically, systems can include joystick controls for operating the steerable catheters and can include controls for rotating the angle at which the distal end of the catheter bends. Other modifications and additions can be made to the control mechanism/handle without departing from the scope of the invention. In some embodiments, the control mechanism/handle controls therapeutic-delivery functionalities, steering of the catheter, electrophysiology electrodes, electroporation electrodes, sonoporation devices, an orientation/isolation balloon, and any other functions that are understood by one in the art.

In some embodiments, the present invention provides a catheter comprising an inner lumen. In some embodiments, a catheter comprises one or more inner lumens (e.g. 1, 2, 3, 4, 5, 6, 7, 8 inner lumens). In some embodiments, the inner lumen runs the length of the catheter shaft. In some embodiments, the lumen is configured to contain one or more therapeutic agents. In some embodiments, the lumen is configured for delivery of one or more therapeutic agents. In some embodiments, the lumen may be of any suitable diameter. In some embodiments, the lumen diameter is maximized with respect to the outer catheter diameter. In some embodiments, the lumen size is irrespective of the outer catheter diameter (e.g. significantly smaller inner lumen than outer catheter diameter). In some embodiments, an inner lumen diameter is 0.1 mm to 12 mm (e.g. 0.1 mm . . . 0.2 mm . . . 0.5 mm . . . 1.0 mm . . . 2.0 mm . . . 5.0 mm . . . 10 mm . . . 12.0 mm, and diameters therein). In some embodiments, a catheter comprises a plurality of inner lumens (U.S. Pat. No. 7,037,290, herein incorporated by reference in its entirety). In some embodiments, catheter lumens are configured for therapeutic delivery, therapeutic storage, encasing electrophysiology devices, encasing electronics, providing catheter steering/movement elements, interacting with a catheter balloon element, etc. In some embodiments, a catheter comprises multiple lumens configured for multiple functions.

In some embodiments, the present invention comprises a balloon (e.g. isolation balloon, electroporation balloon, orientation balloon, ultrasound balloon, etc.). In some embodiments, the present invention comprises a balloon which provides one or more functionalities including, but not limited to, physical isolation of catheter from tissues, thermal isolation of tissues (e.g. isolation of tissues that aren't the intended site of energy delivery), enhancing surface area of electrodes, positioning electrodes around delivery site, acting as a pseudo-electrode, orienting the catheter tip at the delivery site, providing pressure between electrodes and delivery site, delivering ultrasound energy, opening potential-spaces ahead of the catheter tip, etc. In some embodiments, a balloon is located at or near the catheter tip. In some embodiments, the balloon may be positioned anywhere along the length of the catheter. In some embodiments, multiple balloons (e.g. 2, 3, 4, 5, 6, 7, 8, 9, 10 . . . 20 . . . 50, etc.) are positioned along the length of a catheter. In embodiments comprising multiple balloons, the balloons may be of the same or different sizes and/or shapes. In some embodiments, a balloon associated with a catheter of the present invention is of any useful shape (e.g. round, oval, flat, cylindrical, etc.) and/or size. In some embodiments, a balloon is a flat pancake-shape (i.e., the depth is less than the width; e.g., by a ratio of 2:1, 3:1, 4:1, 5:1, 6:1, 7:1, 8:1, 9:1, 10:1, 20:1, etc.). In some embodiments, the balloon is a standard inflatable percutaneous intervention balloon (e.g., a venoplasty balloon). In some embodiments, a pancake-shaped balloon is wider than it is deep (e.g., 1.5× wider than deep; 2× wider than deep; 5× wider than deep; 10× wider than deep; 25× wider than deep). In some embodiments, a balloon is tall and narrow (e.g., 1.5× taller than wide; 2× taller than wide; 3× taller than wide; 5× taller than wide; 10× taller than wide; 25× taller than wide). In some embodiments, a balloon has dimensions (height, width, and/or length) of approximately 1-50 mm (e.g. 1 mm . . . 2 mm . . . 5 mm . . . 10 mm . . . 20 mm . . . 30 mm . . . 40 mm . . . 50 mm). In some embodiments, the height, width, and/or length of a balloon comprise the same dimensions or different dimensions. In some embodiments, the balloon is filled with fluid (e.g. gas or liquid). In some embodiments, the balloon is saline filled. In some embodiments, the balloon is configured for active saline exchange to provide additional thermal protection. In some embodiments, a balloon surrounds the catheter, allowing the catheter to deliver material through a lumen running within the balloon. In some embodiments, the lumen of the catheter and inside of the balloon are provided as separate spaces. In some embodiments, fluids (e.g. liquids or gasses) within the catheter lumen cannot pass into the balloon. In some embodiments, fluids (e.g. liquids or gasses) within the balloon's interior cannot pass into the catheter lumen. In some embodiments, a catheter comprises an inflation lumen, separate from the delivery lumen of the catheter, configured to deliver one or more fluids (e.g. liquids and/or gasses) to inflate the balloon within a subject and/or adjacent to a delivery site. In some embodiments, the balloon may be partially or fully inflated or deflated.

In some embodiments the present invention comprises a balloon configured for isolation and/or orientation of the catheter. In some embodiments, an orientation balloon, isolation balloon, and/or isolation/orientation balloon is provided. In some embodiments, the balloon is configured to adjust to the shape of a tissue region. In some embodiments, the balloon is configured to maintain the proper orientation of the catheter within the desired location. In some embodiments, the balloon is configured to isolate the delivery site from surrounding tissues and structures. In some embodiments, a balloon is configured to physically isolate the catheter tip from surrounding tissues (e.g. non-delivery-site tissues). In some embodiments, the balloon physically moves surrounding tissue or structures away from the delivery site. In some embodiments the balloon is configured to provide a thermal barrier that will minimize damage to adjacent tissue and structures from thermal radiant energy (e.g. during electroporation or ultrasound application). In some embodiments, a balloon thermally isolates surrounding tissues (e.g. non-delivery-site tissues) from the catheter tip. In some embodiments, the balloon provides pressure between tissue at the delivery site and the catheter elements (e.g. electrodes, sonoporation element). In some embodiments, the balloon provides pressure between tissue at the delivery site and the catheter elements (e.g. electrodes, piezoelectric crystals, injection needle, etc.) to enhance the effect of energy delivery or material delivery.

Figure 10:
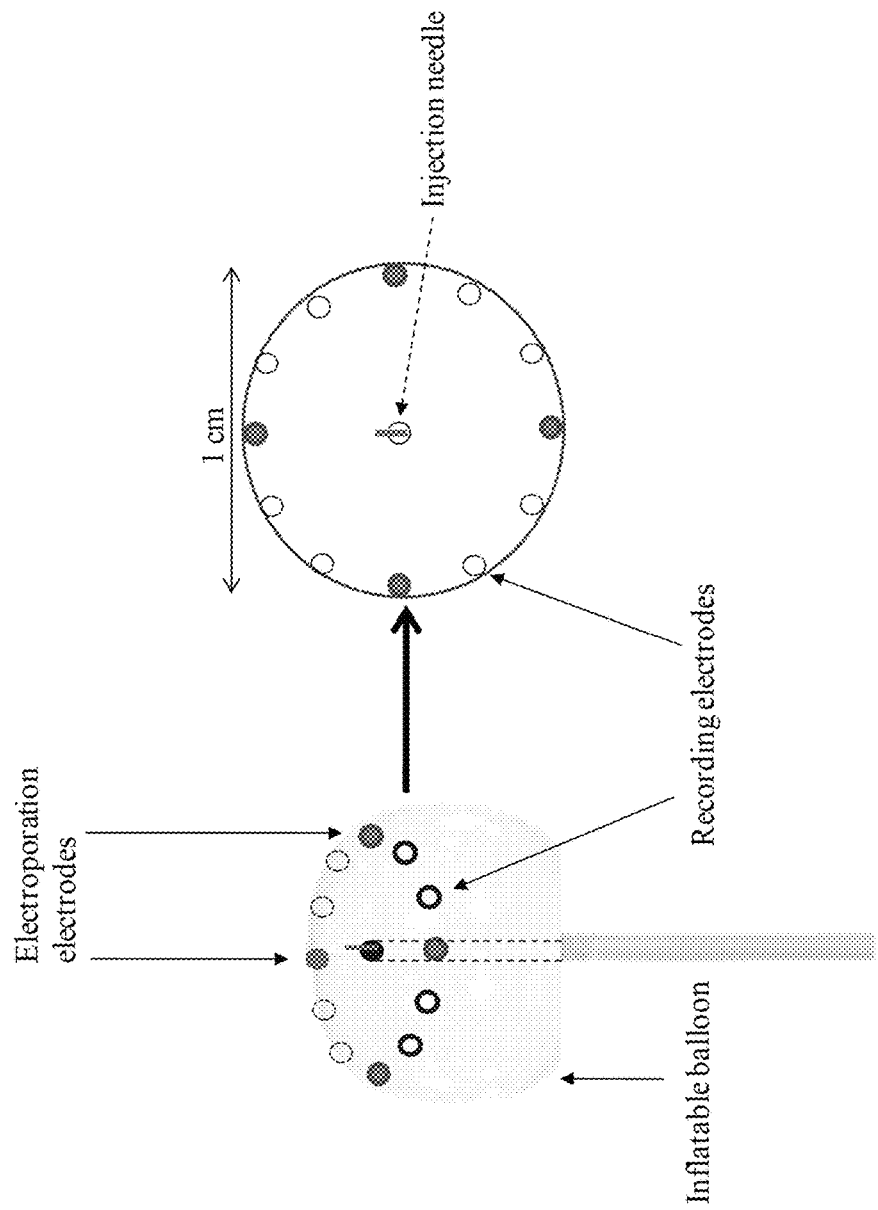
FIG. 10 shows an exemplary catheter and electroporation balloon of the present invention.

In some embodiments, the present invention provides a balloon configured to deliver electroporation energy, sonoporation energy, and/or monitor electrical signals. In some embodiments, an electroporation balloon is provided (SEE FIG. 10). In some embodiments, a sonoporation balloon is provided. In some embodiments, an electroporation balloon is located at the distal end of a catheter. In some embodiments, one or more electrodes (e.g. electroporation electrodes, monitoring electrodes, etc.) are mounted on or in an electroporation balloon (e.g. 1 electrode, 2 electrodes, 3 electrodes, 4 electrodes, 5 electrodes . . . 10 electrodes . . . 20 electrodes . . . 30 electrodes . . . 50 electrodes . . . 100 electrodes, etc.). In some embodiments, one or more (e.g. 1, 2, 3, 4, 5 . . . 10 . . . 20 . . . 50 . . . 100, etc.) electroporation electrodes are mounted on and/or in an electroporation balloon. In some embodiments, electroporation electrodes (e.g. 1 electrode, 2 electrodes, 3 electrodes, 4 electrodes, 5 electrodes . . . 10 electrodes . . . 20 electrodes . . . 30 electrodes . . . 50 electrodes . . . 100 electrodes, etc.) are equally spaced along a ring around the distal end of the catheter (e.g. catheter opening, injection needle, etc.). In some embodiments, one or more monitoring electrodes are located between each set of electroporation electrodes. In some embodiments, one or more (e.g. 1, 2, 3, 4, 5 . . . 10 . . . 20 . . . 50 . . . 100) monitoring electrodes are mounted on and/or in an electroporation balloon. In some embodiments a combination of monitoring and electroporation electrodes are mounted on and/or in an electroporation balloon. In some embodiments, electrodes mounted on an electroporation balloon are configured to adopt a defined pattern (e.g. circle, oval, line, etc.) when the electroporation balloon is inflated and/or substantially inflated. In some embodiments, an inflated electroporation balloon places electrodes in direct contact with tissue at the delivery site. In some embodiments, an inflated electroporation balloon places electrodes in direct contact with tissue surrounding the delivery site. In some embodiments, an inflated electroporation balloon places electrodes in direct contact with delivery site tissue while protecting non-delivery-site tissue. In some embodiments, electrodes are positioned around the catheter opening at the distal end of a catheter (e.g. delivery or injection end of a catheter). In some embodiments, when an electroporation balloon is inflated, electrodes form a ring around the delivery end (e.g. injection needle) of the catheter. In some embodiments, the ring of electrodes on an inflated electroporation balloon is of any suitable diameter (e.g. 2 mm . . . 5 mm . . . 1 cm . . . 2 cm . . . 5 cm, etc.). In some embodiments, the ring of electrodes on an inflated electroporation balloon is of any suitable interelectrode diameter (e.g. 2 mm . . . 5 mm . . . 1 cm . . . 2 cm . . . 5 cm, etc.). In some embodiments, electroporation electrodes and monitoring electrodes form a single ring. In some embodiments, a ring of monitoring electrodes is provided. In some embodiments, a ring of electroporation electrodes is provided. In some embodiments, an electroporation balloon enhances, increases, and/or expands the area of contact between the electrodes and the delivery-site tissue (e.g. myocardium). In some embodiments, an electroporation balloon, when inflated and in contact with delivery-site tissue (e.g. atrial myocardium), allow the monitoring electrodes to record electric activity (e.g. atrial activity) from several sites over its contact area. In some embodiments, gene injection is performed from the catheter within the ring of electrodes around the circumference of the expanded (e.g. inflated) electroporation balloon. In some embodiments, an electroporation balloon also provides isolation (e.g. physical, thermal, etc.) and/or orientation functions.

Figure 11:
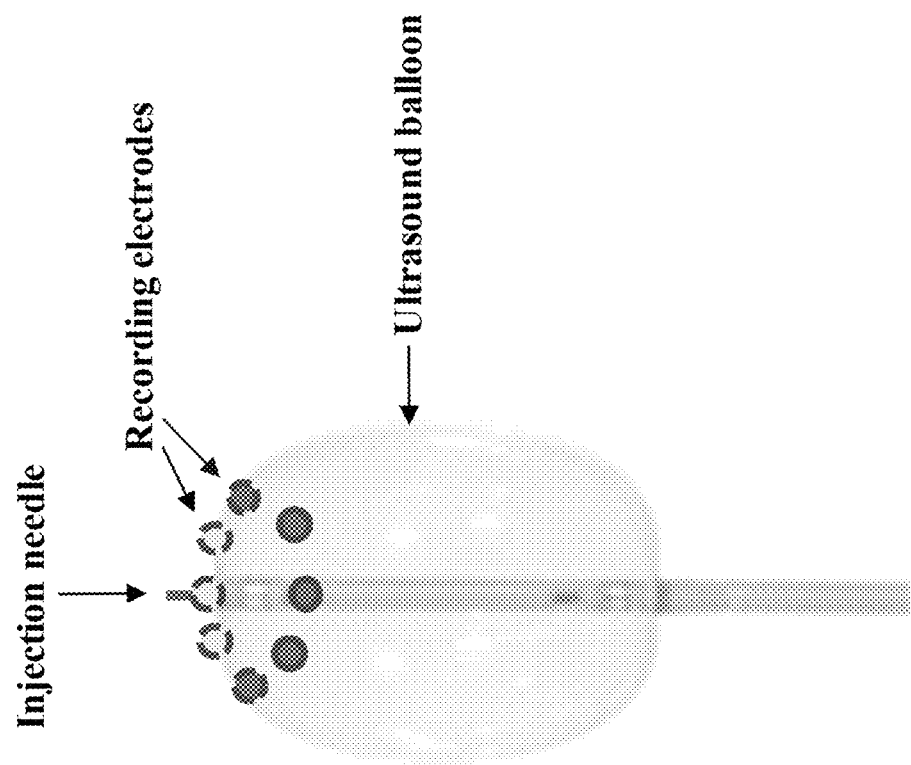
FIG. 11 shows an exemplary catheter and ultrasound balloon of the present invention.

In some embodiments, the present invention provides a balloon configured to deliver ultrasound energy and/or monitor electrical signals. In some embodiments, an ultrasound balloon is provided (SEE FIG. 11). In some embodiments, an ultrasound balloon provides ultrasound energy to surrounding tissues. In some embodiments, an ultrasound balloon provides ultrasound energy to tissues at the delivery site. In some embodiments, an ultrasound balloon provides ultrasound energy to facilitate gene transfer into surrounding tissues. In some embodiments, piezoelectric crystals are housed in, within, and/or on an ultrasound balloon. In some embodiments, piezoelectric ceramics are housed in, within, and/or on an ultrasound balloon. In some embodiments, electric current is applied to piezoelectric crystals to generate ultrasound energy. In some embodiments, ultrasound energy is used to enhance and/or facilitate gene transfer. In some embodiments, ultrasound energy is delivered to the delivery site to enhance and/or facilitate gene transfer (e.g. at the myocardium). In some embodiments, a device comprising an ultrasound balloon provides ultrasound-mediated gene transfer, a technique which is understood in the field (Yoon and Park. Expert Opin Drug Deliv. 2010 March; 7(3):321-30.; Wells. Cell Biol Toxicol. 2010 February; 26(1):21-8.; herein incorporated by reference in their entireties). In some embodiments a combination of monitoring electrodes and ultrasound crystals are mounted on and/or in an ultrasound balloon. In some embodiments, ultrasound crystals mounted on an ultrasound balloon are configured to adopt a defined pattern (e.g. circle, oval, line, etc.) when the ultrasound balloon is inflated and/or substantially inflated. In some embodiments, an inflated ultrasound balloon places piezoelectric crystals in direct contact with tissue at the delivery site. In some embodiments, an inflated ultrasound balloon places piezoelectric crystals in direct contact with tissue surrounding the delivery site. In some embodiments, an inflated ultrasound balloon places piezoelectric crystals in direct contact with delivery site tissue while protecting non-delivery-site tissue. In some embodiments, piezoelectric crystals are positioned around the catheter opening at the distal end of a catheter (e.g. delivery or injection end of a catheter). In some embodiments, when an ultrasound balloon is inflated, piezoelectric crystals are positioned around the delivery end (e.g. injection needle) of the catheter. In some embodiments, the field of piezoelectric crystals on an inflated ultrasound balloon is of any suitable diameter (e.g. 2 mm ... 5 mm ... 1 cm ... 2 cm ... 5 cm, etc.). In some embodiments, monitoring electrodes are located within, at the perimeter of, or near the field of piezoelectric crystals. In some embodiments, an ultrasound balloon enhances, increases, and/or expands the area of contact between the piezoelectric crystals and the delivery-site tissue (e.g. myocardium). In some embodiments, an ultrasound balloon, when inflated and in contact with delivery-site tissue (e.g. atrial myocardium), allows the monitoring electrodes to record electric activity (e.g. atrial activity) from several sites over its contact area. In some embodiments, gene injection is performed from the catheter within the field of piezoelectric crystals around the circumference of the expanded (e.g. inflated) ultrasound balloon. In some embodiments, an ultrasound balloon also provides isolation (e.g. physical, thermal, etc.) and/or orientation functions.

In some embodiments, the present invention provides a catheter for delivering an energy-delivery probe (e.g., electroporation probe, sonoporation probe, etc.) to a site within the body in order to perform electroporation and/or sonoporation at the site. In some embodiments, the present invention provides electroporation and/or sonoporation at the site of therapeutic delivery within a subject. In some embodiments, a catheter provides both electroporation and therapeutic delivery. In some embodiments, a catheter provides both sonoporation and therapeutic delivery. In some embodiments, a catheter provides both electroporation and sonoporation. In some embodiments, a catheter provides sonoporation, electroporation, and therapeutic delivery. In some embodiments, the catheter is configured to carry an energy-delivery probe (e.g., electroporation probe, sonoporation probe, etc.) near the distal end of the catheter. In some embodiments, the catheter and energy-delivery probe (e.g., electroporation probe, sonoporation probe, etc.) comprise a single unit (e.g. electroporation catheter, sonoporation catheter, etc.). In some embodiments, the catheter comprises means for attaching the energy-delivery probe (e.g., electroporation probe, sonoporation probe, etc.). In some embodiments, the energy-delivery probe (e.g., electroporation probe, sonoporation probe, etc.) is located on the distal end of the catheter. In some embodiments, the energy-delivery probe (e.g., electroporation probe, sonoporation probe, etc.) is delivered to the body site where electroporation and/or sonoporation are to be performed. In some embodiments, the distal end of the catheter is positioned over tissue at the electroporation site. In some embodiments, a catheter delivers the electroporation and/or sonoporation energy to the tissue in contact therewith. In some embodiments, a catheter may be essentially straight although it may also be curved or define a closed loop. In some embodiments, the utility for delivering energy (e.g., electric energy, ultrasound energy, etc.) to the catheter is either linked to the catheter or is associated therewith in an induction association to permit the delivery of energy to the catheter. A person versed in the art is able to determine both the intensity of the energy (e.g., electric energy, ultrasound energy, etc.) and the length of time for its application. This may be determined, for example, on the basis of either the scientific literature relating to such techniques, the operators own experience, or through empirical testing.

In some embodiments, the present invention provides a catheter for delivering an ultrasound probe (e.g., sonoporation probe) to a site within the body in order to perform ultrasound-mediated therapeutic transfer at the site (e.g. ultrasound-mediated gene transfer, sonoporation, etc.). In some embodiments, the present invention provides ultrasound at the site of therapeutic delivery within a subject. In some embodiments, a catheter provides both ultrasound and therapeutic delivery (e.g. gene delivery). In some embodiments, the catheter is configured to carry an ultrasound probe (e.g. ultrasound balloon, sonoporation probe, etc.) near the distal end of the catheter. In some embodiments, the catheter and probe comprise a single unit (e.g. ultrasound catheter). In some embodiments, the catheter comprises means for attaching the ultrasound probe (e.g. delivery catheter and ultrasound probe). In some embodiments, the ultrasound probe (e.g. ultrasound balloon) is located on the distal end of the catheter. In some embodiments, the ultrasound probe (e.g. ultrasound balloon) is delivered to the body site where ultrasound application is to be performed. In some embodiments, the distal end of the catheter is positioned over tissue at the ultrasound-application site. In some embodiments, the ultrasound catheter delivers the ultrasound energy to the tissue in contact therewith. In some embodiments, the ultrasound catheter may be essentially straight although it may also be curved or define a closed loop. In some embodiments, the utility for delivering ultrasound energy to the catheter is either linked to the catheter or is associated therewith in an induction association to permit the delivery of ultrasound energy to the catheter. A person versed in the art is able to determine both the intensity of the ultrasound energy and the length of time for its application. This may be determined, for example, on the basis of either the scientific literature relating to ultrasound-mediate gene transfer techniques, or the operators own experience.

In some embodiments, the present invention provides a catheter for delivering an electroporation probe to a site within the body in order to perform electroporation-mediated therapeutic transfer at the site (e.g. electroporation-mediated gene transfer). In some embodiments, the present invention provides electroporation at the site of therapeutic delivery within a subject. In some embodiments, a catheter provides both electroporation and therapeutic delivery (e.g.

gene delivery). In some embodiments, the catheter is configured to carry an electroporation probe near the distal end of the catheter. In some embodiments, the catheter and probe comprise a single unit (e.g. electroporation catheter). In some embodiments, the catheter comprises means for attaching the electroporation probe (e.g. delivery catheter and electroporation probe). In some embodiments, the electroporation probe is located on the distal end of the catheter. In some embodiments, the electroporation probe is delivered to the body site where ultrasound application is to be performed. In some embodiments, the distal end of the catheter is positioned over tissue at the electroporation-application site. In some embodiments, the electroporation catheter delivers the electric energy to the tissue in contact therewith. In some embodiments, the electroporation catheter may be essentially straight although it may also be curved or define a closed loop. In some embodiments, the utility for delivering electric energy to the catheter is either linked to the catheter or is associated therewith in an induction association to permit the delivery of electric energy to the catheter. A person versed in the art is able to determine both the intensity of the electric energy and the length of time for its application. This may be determined, for example, on the basis of either the scientific literature relating to ultrasound-mediate gene transfer techniques, or the operators own experience.

In some embodiments, the present invention provides a catheter for delivering an electrophysiology probe to a site within the body in order to record or monitor electrical signals at the site. In some embodiments, the present invention records or monitors electrical signals at the site of therapeutic delivery within a subject. In some embodiments, a catheter provides both electrophysiology recordation and therapeutic delivery. In some embodiments, the catheter is configured to carry an electrophysiology probe near the distal end of the catheter. In some embodiments, the catheter and probe comprise a single unit (e.g. electrophysiology catheter). In some embodiments, the catheter comprises means for attaching the electrophysiology probe (e.g. delivery catheter and electrophysiology probe). In some embodiments, the electrophysiology probe is located on the distal end of the catheter. In some embodiments, the electrophysiology probe is delivered to the body site where recording of electrical signals is to be performed. In some embodiments, the distal end of the catheter is positioned over tissue at the electrophysiologic monitoring site. In some embodiments, the electrophysiology catheter records the electrophysiology energy of the tissue in contact therewith. In some embodiments, the utility for recording electrophysiology energy is either linked to the catheter or is associated therewith. A person versed in the art is able to determine techniques and means for recording electrical signals within a subject This may be determined, for example, on the basis of either the scientific literature relating to electrophysiology techniques, or the operators own experience.

In some embodiments, the present invention provides delivery of therapeutics (e.g. pharmaceuticals, gene therapy, small molecules, nucleic acid, peptides, etc.). In some embodiments, catheter devices provide a delivery means for localized administration of therapeutics, thereby reducing side effects from systemic administration. In some embodiments, therapeutics of the present invention comprise small molecule drugs, peptides, nucleic acids (e.g. DNA, RNA, genes, minigenes, RNAi, etc.). In some embodiments, the present invention finds utility in the targeted delivery of gene therapy reagents (e.g. DNA, minigenes, naked DNA, viral vector, etc.). In some embodiments, precise placement of gene therapy reagents increases efficiency of their incorporation into cells and/or their effectiveness in treating a disease or disorder. In some embodiments, the present invention utilizes electroporation and/or sonoporation to facilitate therapeutic uptake into target cells. In some embodiments, the present invention utilizes electroporation and/or sonoporation to increase the efficiency of therapeutic uptake into target cells. In some embodiments, the present invention provides electroporation and/or sonoporation in conjunction with gene therapy (e.g. delivery of DNA (e.g. naked DNA). In some embodiments, electroporation and/or sonoporation increases the efficiency of gene delivery in gene therapy. In some embodiments, electroporation in and/or sonoporation conjunction with gene therapy increases the treatment effectiveness of the gene therapy treatment. In some embodiments, electroporation and/or sonoporation enhances gene transfer. In some embodiments, electroporation enhances entry of therapeutics (e.g. gene therapy reagents, nucleic acid, peptides, minigenes, DNA, etc.) into target cells. In some embodiments, the present invention utilizes electric and/or ultrasound energy to facilitate therapeutic uptake into target cells. In some embodiments, the present invention utilizes electric and/or ultrasound energy to increase the efficiency of therapeutic uptake into target cells. In some embodiments, the present invention provides application of electric and/or ultrasound energy in conjunction with gene therapy (e.g. delivery of DNA (e.g. naked DNA). In some embodiments, ultrasound energy increases the efficiency of gene delivery in gene therapy. In some embodiments, application of electric and/or ultrasound energy in conjunction with gene therapy increases the treatment effectiveness of the gene therapy treatment. In some embodiments, application of electric and/or ultrasound energy enhances gene transfer. In some embodiments, application of electric and/or ultrasound energy enhances entry of therapeutics (e.g. gene therapy reagents, nucleic acid, peptides, minigenes, DNA, etc.) into target cells.

In some embodiments, the present invention provides a means for treating a subject. In some embodiments, catheters of the present invention provide therapeutic delivery and electroporation and/or sonoporation to treat a subject. In some embodiments, catheters of the present invention provide therapeutic delivery and application of electric and/or ultrasound energy to treat a subject. In some embodiments, the present invention provides localized treatment. In some embodiments, use of the present invention avoids systemic delivery of therapeutics, instead delivering therapeutics to the desired site of action. In some embodiments, electroporation and/or sonoporation increases the efficiency of therapeutic uptake into cells. In some embodiments, electroporation and/or sonoporation increase the efficiency of gene therapy. In some embodiments, a device introduces an electric current (e.g. 0.5 to 1 V) to a therapeutic delivery site. In some embodiments, electroporation increases the permeability of the cells in the local region of the electric current. In some embodiments, sonoporation increases the permeability of the cells in the local region of the ultrasound energy. In some embodiments, electroporated and/or sonoporated cells are more readily available for uptake of therapeutics (e.g. DNA). In some embodiments, monitoring of electrical signals before and after administration of therapeutics, sonoporation, and/or electroporation provides a method for monitoring the effectiveness of treatment. In some embodiments, electrophysiology results allow clinicians to monitor the course of treatment or treatments using a device of the present invention and/or other medical treatments.

The catheter shaft can be of any suitable construction and made of any suitable material. In some embodiments, devices, systems, and/or components of the present invention comprise materials such as CoCrMo alloy, Titanium alloy, cpTi, Ti6Al4V ELI medical grade stainless steel, Tantalum, Tantalum alloy, Nitinol, polymers, alloys, metals, ceramics, oxides, minerals, glasses and combinations thereof. In preferred embodiments, materials are selected based on desirability of biomechanical properties and interaction with surrounding biological environment of the device and/or system. In some embodiments, materials are selected based on the specific application, requirements, and/or deployment location. In some embodiments, devices, systems, and/or other components of the present invention comprise one or more metals, alloys, plastics, polymers, natural materials, synthetic materials, fabrics, etc. In some embodiments, devices, systems, and/or other components of the present invention comprise one or more metals including but not limited to aluminum, antimony, boron, cadmium, cesium, chromium, cobalt, copper, gold, iron, lead, lithium, manganese, mercury, molybdenum, nickel, platinum, palladium, rhodium, silver, tin, titanium, tungsten, vanadium, and zinc. In some embodiments, devices, systems, and/or other components of systems of the present invention comprise one or more alloys including but not limited to alloys of aluminium (e.g., Al—Li, alumel, duralumin, magnox, zamak, etc.), alloys of iron (e.g., steel, stainless steel, surgical stainless steel, silicon steel, tool steel, cast iron, Spiegeleisen, etc.), alloys of cobalt (e.g., stellite, talonite, etc.), alloys of nickel (e.g., German silver, chromel, mumetal, monel metal, nichrome, nicrosil, nisil, nitinol, etc.), alloys of copper (beryllium copper, billon, brass, bronze, phosphor bronze, constantan, cupronickel, bell metal, Devarda's alloy, gilding metal, nickel silver, nordic gold, prince's metal, tumbaga, etc.), alloys of silver (e.g., sterling silver, etc.), alloys of tin (e.g., Britannium, pewter, solder, etc.), alloys of gold (electrum, white gold, etc.), amalgam, and alloys of lead (e.g., solder, terne, type meta, etc.). In some embodiments, devices, systems, and/or other components of the present invention comprise one or more plastics including but not limited to Bakelite, neoprene, nylon, PVC, polystyrene, polyacrylonitrile, PVB, silicone, rubber, polyamide, synthetic rubber, vulcanized rubber, acrylic, polyethylene, polypropylene, polyethylene terephthalate, polytetrafluoroethylene, gore-tex, polycarbonate, etc. In some embodiments, elements of a device of the present invention may also comprise glass, textiles (e.g., from animal, plant, mineral, and/or synthetic sources), liquids, etc. In some embodiments, a suitable construction includes, but is not limited to, an outer wall made of polyurethane, TEFLON, HDPE, nylon, PEEK, PTFE, PEBAX, or other suitable materials.

In some embodiments, a catheter of the present invention is inserted into a lumen within a subject (e.g., vein, artery, gastrointestinal tract, lumen of an organ, etc.) and/or maneuvered through a lumen of a subject. In some embodiments, a catheter of the present invention is inserted into an artery of a subject and/or maneuvered through an artery of a subject. In some embodiments, a catheter of the present invention is inserted into and/or maneuvered through an artery or arteries including, for example, the ascending aorta, right coronary artery, left coronary artery, anterior interventricular, circumflex, left marginal arteries, posterolateral artery, intermedius, arch of aorta, brachiocephalic artery, common carotid artery, internal carotid artery, external carotid artery, subclavian artery, vertebral artery, internal thoracic artery, thyrocervical trunk, deep cervical artery, dorsal scapular artery, brachial artery, thoracic aorta, abdominal aorta, inferior phrenic, celiac, superior mesenteric, middle suprarenal, renal, anterior and posterior, interlobar artery, gonadal, lumbar, inferior mesenteric, median sacral, common iliac, common iliac arteries, internal iliac artery, anterior division, obturator artery, superior vesical artery, vaginal artery (females), inferior vesical artery (males), middle rectal artery, internal pudendal artery, inferior gluteal artery, uterine artery (females), deferential artery (males), (obliterated) umbilical artery, posterior division, iliolumbar artery, lateral sacral artery, superior gluteal artery, external iliac artery, inferior epigastric artery, deep circumflex iliac artery, femoral artery, superficial epigastric artery, superficial circumflex iliac artery, superficial external pudendal artery, deep external pudendal artery, deep femoral artery, descending genicular artery, popliteal artery, anterior tibial artery, posterior tibial artery, sural artery, medial superior genicular artery, lateral superior genicular artery, middle genicular artery, inferior lateral, and inferior medial genicular artery. In some embodiments, a catheter of the present invention is inserted into a vein of a subject and/or maneuvered through a vein of a subject. In some embodiments, a catheter of the present invention is inserted into and/or maneuvered through an vein or veins including, for example, the internal jugular, external jugular, subclavian, axillary, cephalic, brachial, basilica, radial, ulnar, renal, brachiocephalic, superior vena cava, hepatic, hepatic portal, common iliac, external iliac, femoral, great saphenous, popliteal, posterior tibial, anterior tibial, small saphenous, dorsal venous arch, etc.

In some embodiments, the present invention provides devices and methods for material delivery (e.g., gene delivery), electroporation, sonoporation, and/or monitoring electrophysiological activity at a tissue (e.g., cardiac tissue, muscle tissue, dermal tissue, etc.), organ (e.g., heart), organ system (circulatory system, digestive tract, nervous system, etc.), etc. In some embodiments, material delivery, electroporation, sonoporation, and/or monitoring electrophysiological activity are performed in one or more layers of the heart (e.g. endocardium, myocardium, epicardium, etc.). In some embodiments, access is provided by devices of the present invention to the endocardium, myocardium, and/or epicardium. In some embodiments, materials (e.g., therapeutics, nucleic acids, etc.) are delivered via devices of the present invention to the endocardium, myocardium, epicardium, etc. In some embodiments, sonoporation and/or electroporation energy are delivered via devices of the present invention to the endocardium, myocardium, and/or epicardium. In some embodiments, the electrophysiological activity of the endocardium, myocardium, and/or epicardium are monitored. In some embodiments, the electrophysiological activity of the endocardium, myocardium, and/or epicardium are monitored following delivery of materials (e.g., therapeutics, nucleic acids, etc.), sonoporation, and/or electroporation. In some embodiments, materials (e.g., therapeutics, nucleic acids, etc.) are delivered to, sonoporation and/or electroporation are applied to, and/or electrophysiological activity is monitored in the endocardium of the heart of subject (e.g., mammal, human, etc.). In some embodiments, the present invention provides devices for targeting endothelial cells (e.g., of the endocardium) with materials (e.g., therapeutics, nucleic acids, etc.), electroporation, sonoporation, and/or electrophysiological activity measurements. In some embodiments, materials (e.g., therapeutics, nucleic acids, etc.) are delivered to, sonoporation and/or electroporation are applied to, and/or electrophysiological activity is monitored in the epicardium of the heart of subject (e.g., mammal, human, etc.). In some embodiments, materials (e.g., therapeutics, nucleic acids, etc.) are delivered to, sonoporation and/or electroporation are applied to, and/or electrophysiological activity is monitored in the myocardium of the heart of subject (e.g., mammal, human, etc.). In some embodiments, materials (e.g., therapeutics, nucleic acids, etc.) are delivered to, sonoporation and/or electroporation are applied to, and/or electrophysiological activity is monitored in non-cardiac (e.g., non-cardiac circulatory system tissues, non-circulatory system tissues and organs, etc.) systems, organs, tissues, and/or cells. In some embodiments, materials (e.g., therapeutics, nucleic acids, etc.) are delivered to, sonoporation and/or electroporation are applied to, and/or electrophysiological activity is monitored in tissues, organs and/or cells in the digestive system (e.g., tissues and/or organs of the alimentary canal), respiratory system (e.g., lungs, etc.), circulatory system (e.g., veins, arteries, etc.), musculoskeletal system (e.g., muscle tissue, connective tissue, etc.), and/or nervous system (e.g., brain, nerves, spinal cord, etc.). In some embodiments, a device of the present invention accesses delivery sites via veins arteries, other body lumens (e.g., digestive tract (e.g., orally, rectally, etc.), subcutaneously, other suitable routes, and combinations thereof.

In some embodiments, the present invention provides devices, compositions, and methods for treatment, diagnosis, or monitoring of diseases and/or conditions. The catheter devices, catheter systems, and methods of the present invention may be used with any subject or patient, including, but not limited to, humans, non-human primates, mammals, feline, canine, bovine, equine, porcine, rodent, etc. In some embodiments, the subject is a human requiring treatment for a medical condition. In some embodiments, the subject is a human or other mammal suffering from a condition, disease, or disorder delivery of a therapeutic agent (e.g. gene therapy) to a specific location within the subject provides treatment. In some embodiments, the subject is a human or other mammal undergoing surgery or catheter based diagnostic or therapeutic procedures. In addition, any body region may be used with the catheter devices, catheter systems, kits, and methods of the present invention.

In some embodiments, the present invention provides devices and methods for treating diseases, disorders and conditions in a subject. In some embodiments, the present invention provides devices and methods for treating diseases and disorders in any body regions or locations that are accessible by catheter. In some embodiments, the present invention provides devices and methods for treating heart conditions (e.g. rhythm disturbances (e.g. atrial fibrillation)). In some embodiments, the present invention provides compositions and methods to treat or prevent conditions and/or diseases of the heart (e.g. rhythm disturbances (e.g. atrial fibrillation)). In some embodiments, the present invention provides treatment or prevention of a heart disease or condition selected from the list of aortic dissection, cardiac arrhythmia (e.g. atrial cardiac arrhythmia (e.g. premature atrial contractions, wandering atrial pacemaker, multifocal atrial tachycardia, atrial flutter, atrial fibrillation, etc.), junctional arrhythmias (e.g. supraventricular tachycardia, AV nodal reentrant tachycardia, paroxysmal supra-ventricular tachycardia, junctional rhythm, junctional tachycardia, premature junctional complex, etc.), atrio-ventricular arrhythmias, ventricular arrhythmias (e.g. premature ventricular contractions, accelerated idioventricular rhythm, monomorphic ventricular tachycardia, polymorphic ventricular tachycardia, ventricular fibrillation, etc.), etc.), congenital heart disease, myocardial infarction, dilated cardiomyopathy, hypertrophic cardiomyopathy, aortic regurgitation, aortic stenosis, mitral regurgitation, mitral stenosis, Ellis-van Creveld syndrome, familial hypertrophic cardiomyopathy, Holt-Orams Syndrome, Marfan Syndrome, Ward-Romano Syndrome, and/or similar diseases and conditions. In some embodiments, the present invention provides methods for blocking G protein coupled receptor mediated signaling for treating atrial fibrillation (see, U.S. application Ser. No. 12/430,595, herein incorporated by reference in its entirety).

Both sympathetic and parasympathetic activity in the heart is mediated by heterotrimeric G-protein (G$\alpha$G$\alpha$3G$\alpha$) coupled pathways initiated by G-protein coupled receptors (GPCRs). In some embodiments, the present invention provides a gene-based approach to selectively inhibit the G-protein signaling pathways. In some embodiments, the present invention is used in an epicardial approach to administer minigenes expressing G-protein inhibitory peptides to the PLA, in order to selectively inhibit the C-terminus of G$\alpha$i and G$\alpha$s in this region. In some embodiments, the present invention provides electroporation and/or ultrasound energy to enhance the effectiveness of gene therapy (e.g., for naked DNA and/or viral vectors). In some embodiments, electroporation and/or ultrasound energy enhance intracellular gene transfer (e.g. within the PLA). In some embodiments, the present invention targets G-protein mediated autonomic signaling, and/or other key signal transduction pathways (e.g. the TGF-beta pathway in the creation of atrial fibrosis). In some embodiments, the present invention provides a targeted gene-based approach to attenuate TGF-beta signaling in the left atrium, in order to decrease the development of fibrosis in AF.

In some embodiments, the present invention provides a non-surgical, minimally invasive approach. In some embodiments, the present invention provides a clinical gene-based approach. In some embodiments, the present invention provides a minimally invasive, transvenous (transseptal) approach to achieve gene delivery (e.g. within the left atrium (e.g. in the PLA)). In some embodiments, the present invention provides safe and effective gene delivery (e.g. to the atrium) via a percutaneous, transvenous approach. In some embodiments, the present invention provides delivery of therapeutics including gene-base therapies, cell-based therapies, or pharmacological therapies. In some embodiments, the present invention provides electroporation as an efficient method for transfer of naked DNA into cells (e.g. in the PLA). In some embodiments, the present invention provides application of ultrasound energy as an efficient method for transfer of naked DNA into cells (e.g. in the PLA). In some embodiments, the present invention provides targeted and efficient gene transfer (e.g. in the PLA) via a transvenous, endocardial approach.

In some embodiments, devices include at least one tissue contacting member for contacting a tissue or organ surface (e.g., epicardial tissue) and securing the device to the surface. In some embodiments, devices include at least one cardiac-contacting member for contacting a cardiac surface (e.g., epicardial tissue, endocardial tissue) and securing the device to the surface. In one aspect, a system for treating heart tissue to treat a cardiac arrhythmia comprises: at least one energy-delivery element for applying energy to the heart tissue; at least one tissue securing member (e.g., clamp, balloon, suction, etc.) coupled with the at least one energy-delivery element for enhancing contact of the energy-delivery element with the heart tissue; and at least one guiding member coupled with at least one of the energy-delivery element and the tissue securing member for guiding the energy-delivery element and the tissue securing member to a location for treating the heart tissue. In some embodiments, treating the heart tissue comprises applying energy to the heart tissue in a pattern to reduce or eliminate the cardiac arrhythmia. In some embodiments, treating the heart tissue comprises applying energy to the heart tissue to aid in therapeutic uptake (e.g., through electroporation and/or sonoporation). The applied energy may be in any suitable form, such as radio frequency energy, ultrasound energy, microwave energy, cryogenic energy, thermoelectric energy or laser energy. In some embodiments, the energy is applied to an epicardial surface of the heart. In some embodiments, the energy is applied to an endocardial surface of the heart. In some embodiments, the energy is applied to an epicardial surface of the heart, wherein the energy is transmitted from the epicardial surface through the heart tissue to an endocardial surface. Optionally, the energy may be further transmitted through fat and/or connective tissue to access the treatment site.

EXPERIMENTAL

Example 1

Denervation of the PLA with Minigene Expressing Gαi Inhibitory Peptide

Experiments were conducted during development of the present invention with minigene expressing Gαi peptide in a model of AF, which demonstrate that epicardial injection (using an open-chest approach) of minigenes expressing Gαi peptides into the PLA followed by electroporation results in: a) successfully transcription of the minigene with production of Gαi peptide and 2) inhibit of vagal responsiveness in the entire left atrium.

High-density epicardial mapping was performed in canine subjects using 2×2 electrodes in the PVs, 7×3 electrodes in the PLA, and 7×3 electrodes in the left atrial appendage (LAA). Effective refractory periods (ERPs) were obtained at baseline and in response vagal stimulation (VS)(20 Hz). After baseline mapping, 1 mg (in a volume of up to 2 ml) of either FLAG-tagged Gαi1/2 expressing minigene, or FLAG-tagged GαR (random peptide) expressing minigene was injected into the PLA. The PLA was then subjected to electroporation using the electrodes (SEE FIG. 1). Epicardial mapping was performed again 48-72 hours after minigene injection. RNA was isolated from frozen heart tissue for PCR and RT-PCR. Western blotting and immunostaining were performed for FLAG-tagged peptide.

Gene Expression in the PLA.

Figure 3:
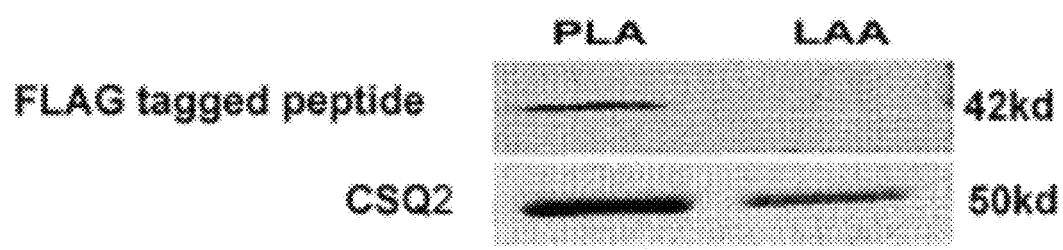
FIG. 3 shows an exemplary Western blot for a FLAG-tagged G$\alpha$i peptide.
Figure 4:
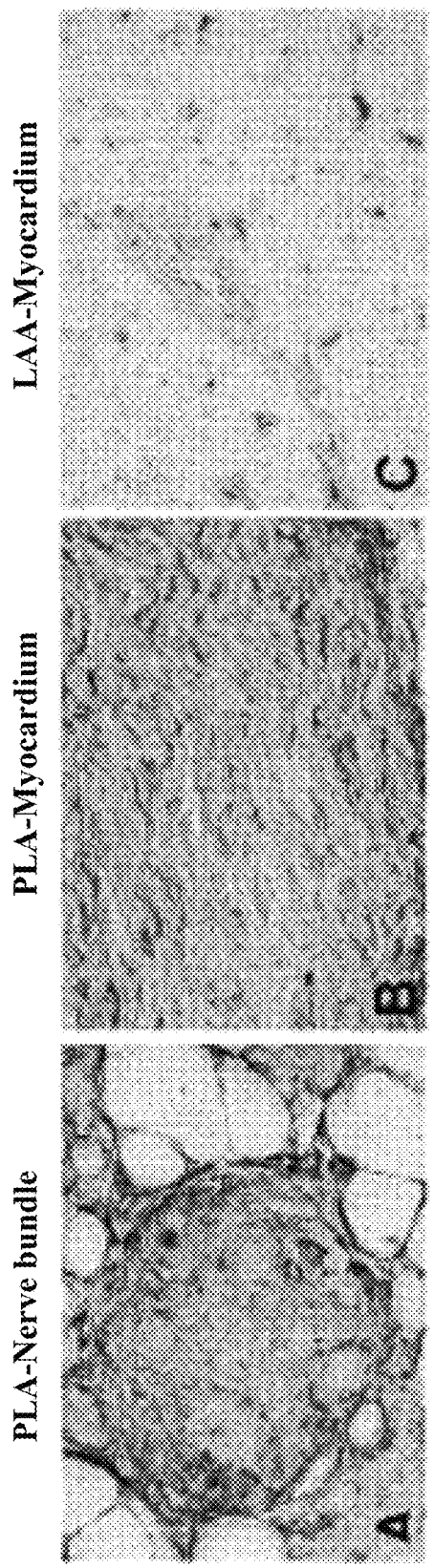
FIG. 4 shows exemplary results of immunostaining for FLAG-tagged G$\alpha$i1/2 peptide.

FIG. 2A shows the results of PCR on PLA tissue injected with the minigene. Lanes 5 shows the presence of minigene mRNA in PLA tissue (434 bp and denoted by arrow), indicating successful transcription of the minigene. FIG. 2B shows the results of RT-PCR; the bar-graph shows expression of the minigene only in the PLA (the site of minigene injection), and not in the LAA (remote from injection site). FIG. 3 shows a representative western blot for FLAG-tagged Gαi peptide. The blot shows expression of FLAG in the PLA (the site of gene injection) but no FLAG expression remote from the site of injection (LAA). FIG. 4 shows the results of immunostaining for FLAG-tagged Gαi1/2 peptide. Peptide expression was noted both in cardiomyocytes as well as in nerve bundles/ganglion cells. Panels A and B show the presence of Gαi peptide in a nerve bundle and in the myocardium of the PLA (heavy brown stain). In contrast, as shown in panel C, there is no peptide, as evidenced by the lack of heavy brown stain in the adjoining LAA, which is remote from gene injection site, therefore serving as a negative control.

Functional Effects of Gαi1/2 Minigene.

Figure 5:
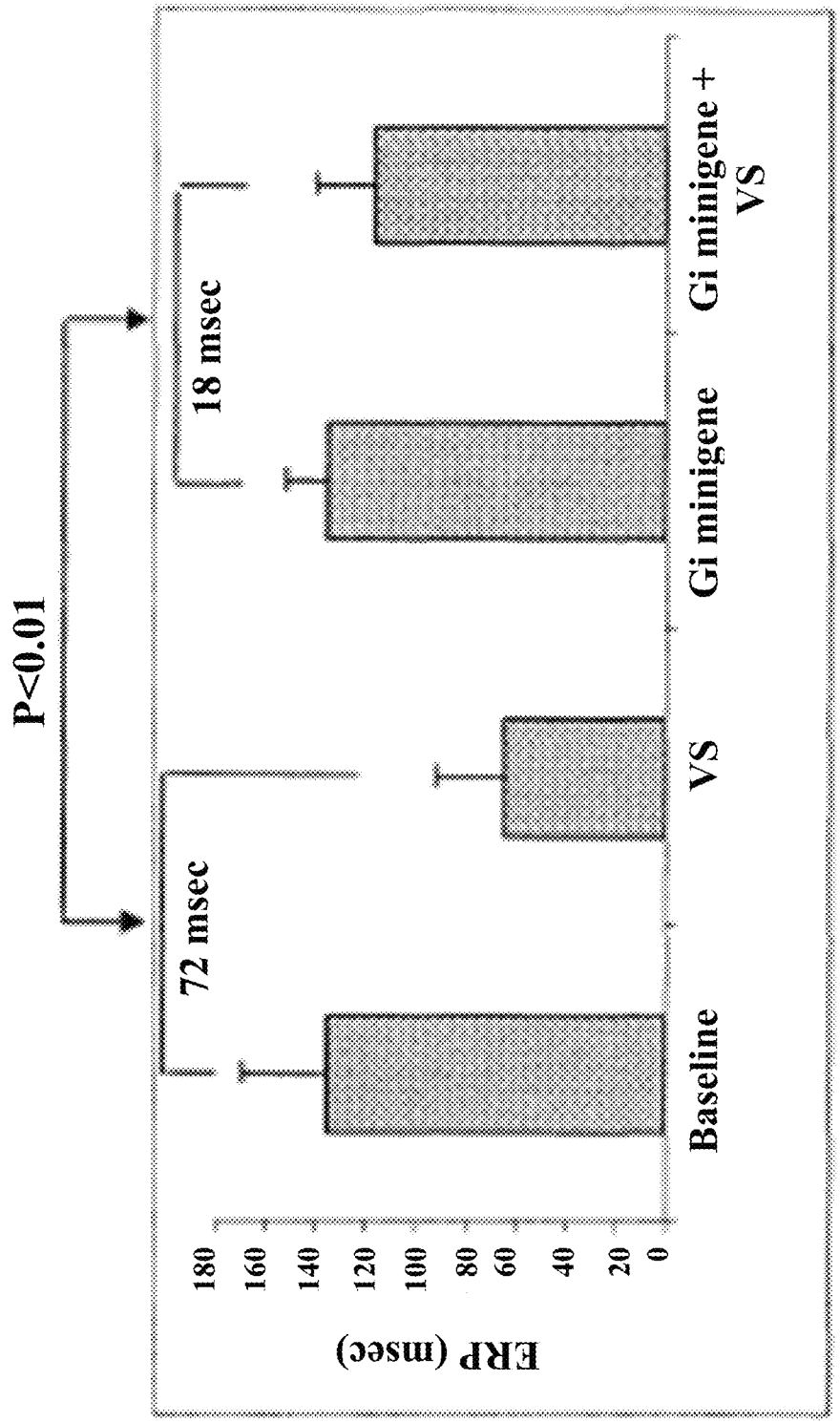
FIG. 5 shows exemplary effects of G$\alpha$i1/2 minigene on vagal-induced ERP shortening.
Figure 6:
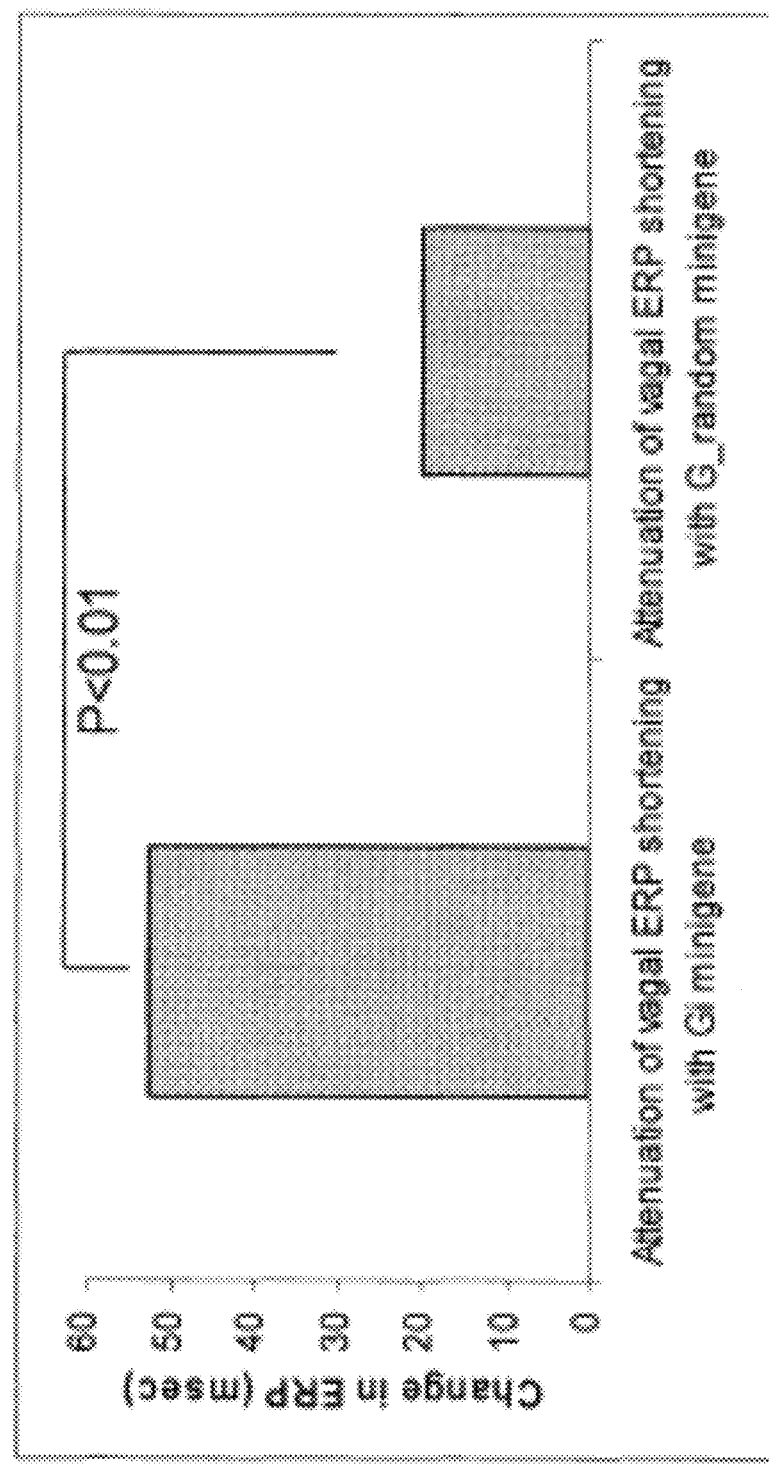
FIG. 6 shows a graph depicting VS-induced ERP shortening in canine subjects receiving G$\alpha$i1/2 and G$\alpha$R (random) minigenes.
Figure 7:
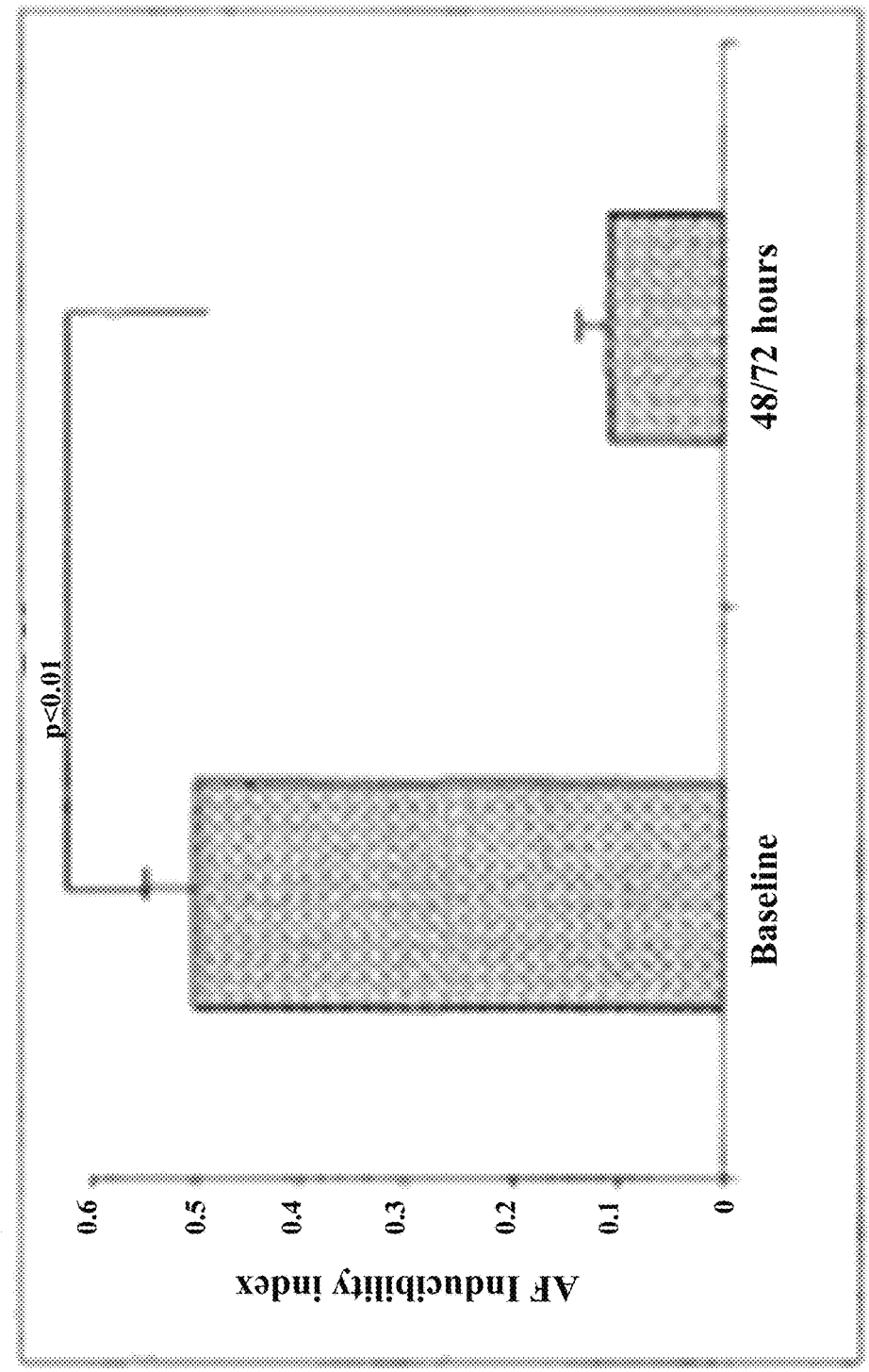
FIG. 7 shows diminishment of vagal-induced AF-inducibility following G$\alpha$i1/2 minigene injection.
Figure 8:
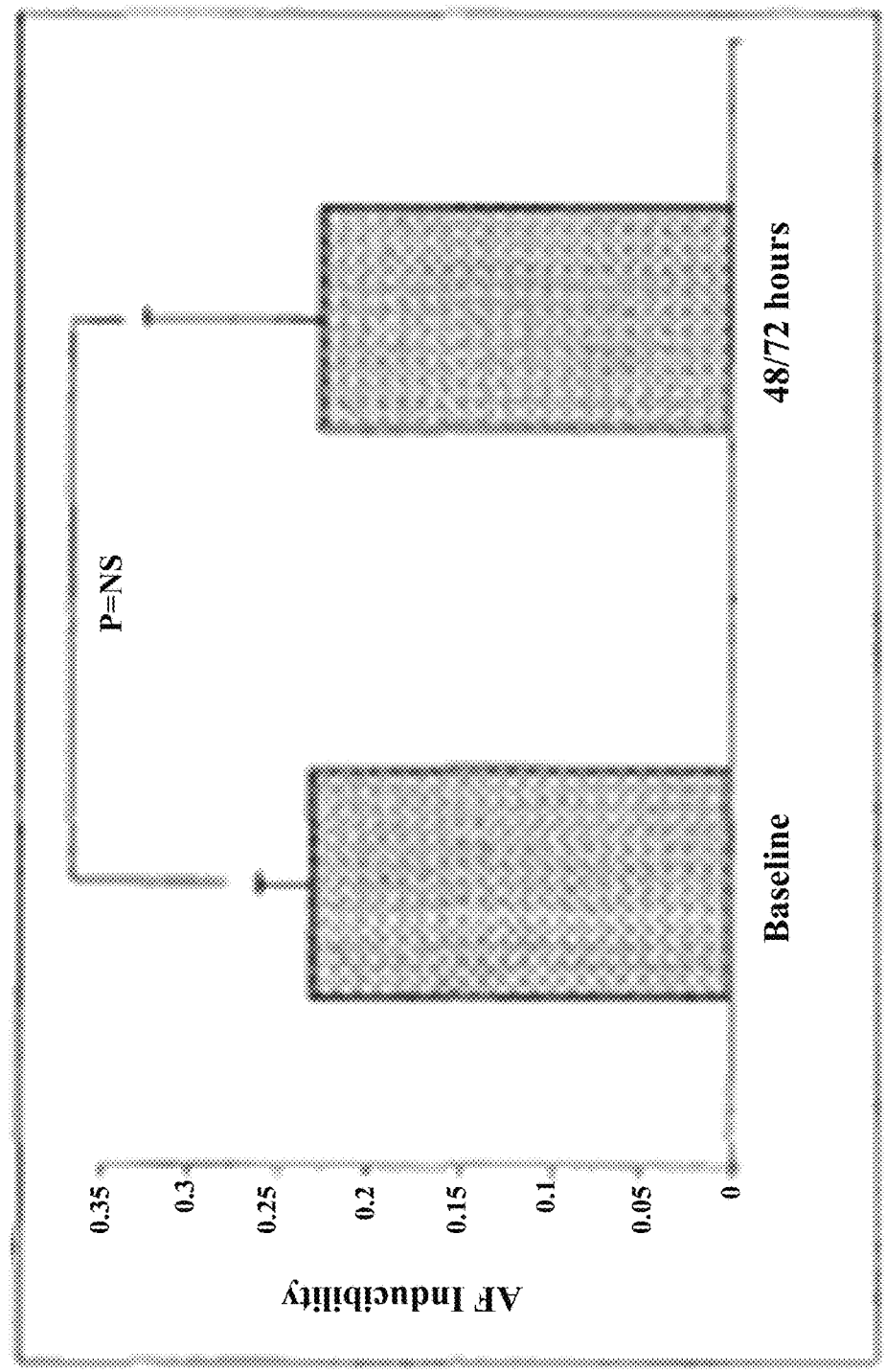
FIG. 8 shows a graph depicting no change in vagal-induced AF-inducibility following G$\alpha$R minigene injection.

FIG. 5 shows the effects of Gαi1/2 minigene on vagal-induced ERP shortening. Significant VS-induced ERP shortening was noted at baseline in each dog. However, VS-induced ERP shortening was markedly attenuated after Gαi minigene injection. Vagal-induced AF inducibility was also significantly diminished after Gα1/2 minigene injection (SEE FIG. 7, left side bar). Although some attenuation of VS-induced ERP shortening was also noted in control dogs receiving GαR minigene, the effect was significantly less than in subjects receiving Gα1/2 minigene (SEE FIG. 6, right side bar). VS-induced AF inducibility was not significantly affected in subjects receiving GαR minigene (SEE FIG. 8).

Experiments performed during development of embodiments, of the present invention demonstrate the feasibility of a gene-based approach in altering AF substrate.

What is claimed is:
1. A method of treating atrial fibrillation in a subject and monitoring the effectiveness of treatment comprising:
   (a) inserting a device into the subject, the device comprising:
      (i) an elongate member with a proximal end, a distal tip, and an inner lumen,
      (ii) an energy-delivery element located at the distal tip of the elongate member, comprising first and second electrodes, and
      (iii) an electrophysiology monitoring element;
   (b) positioning the distal tip of the elongate member at a treatment site on an epicardial or endocardial surface;
   (c) delivering a nucleic acid gene therapy agent to the treatment site through the inner lumen of the elongate member;
   (d) electroporating the treatment site with the first and second electrodes; and
   (e) recording intracardiac electrophysiologic activity with the electrophysiology monitoring element after delivering the nucleic acid gene therapy agent to the treatment site.
2. The method of claim 1, further comprising a step of recording intracardiac electrophysiologic activity before delivering the nucleic acid gene therapy agent to the treatment site.
3. The method of claim 2, further comprising a step of comparing the intracardiac electrophysiologic activity before delivering the nucleic acid gene therapy agent to the treatment site with the intracardiac electrophysiologic activity after delivering the nucleic acid gene therapy agent to the treatment site.

* * * * *